(12) United States Patent
Matsumura et al.

(10) Patent No.: US 7,867,141 B2
(45) Date of Patent: Jan. 11, 2011

(54) PHYSICAL ACTIVITY MEASURING SYSTEM

(75) Inventors: Yoshihiro Matsumura, Kadoma (JP); Matsuki Yamamoto, Ashiya (JP); Hideki Nakamura, Osaka (JP); Yasuko Yamamoto, Osaka (JP); Junji Ikeda, Suita (JP); Masayuki Mitsui, Hikone (JP); Tadaharu Kitadou, Moriguchi (JP); Kazunori Kidera, Matsubara (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 953 days.

(21) Appl. No.: 11/072,403

(22) Filed: Mar. 7, 2005

(65) Prior Publication Data
US 2006/0020174 A1  Jan. 26, 2006

(30) Foreign Application Priority Data
Jul. 21, 2004 (JP) ............................. 2004-213165
Jan. 26, 2005 (JP) ............................. 2005-018679

(51) Int. Cl.
A63B 71/00 (2006.01)
G01C 21/00 (2006.01)

(52) U.S. Cl. .................. 482/8; 482/3; 482/9; 377/24.2

(58) Field of Classification Search ..................... 482/8, 482/1–7, 9, 902, 900
See application file for complete search history.

(56) References Cited

U.S. PATENT DOCUMENTS

| | | | | |
|---|---|---|---|---|
| 4,708,337 A | * | 11/1987 | Shyu | 482/54 |
| 4,828,257 A | * | 5/1989 | Dyer et al. | 482/5 |
| 4,919,418 A | * | 4/1990 | Miller | 482/6 |
| 4,934,694 A | * | 6/1990 | McIntosh | 482/9 |
| 5,451,192 A | * | 9/1995 | Hefele | 482/52 |

(Continued)

FOREIGN PATENT DOCUMENTS

EP   1 256 316 A1   11/2002

(Continued)

OTHER PUBLICATIONS

EPO Search Report dated Oct. 18, 2005.

(Continued)

*Primary Examiner*—Steve R Crow
*Assistant Examiner*—Robert F Long
(74) *Attorney, Agent, or Firm*—Cheng Law Group, PLLC

(57) ABSTRACT

A physical activity measuring system analyzes analyzing body motions of a user to accurately determine the exercise intensity. The system includes a portable device which is adapted to be carried by the user and is equipped with a body sensor and an indicator for indication of the exercise intensity. The body sensor senses the user's body motions to give corresponding motion strength. The portable device has a processor which constitutes an exercise calculator which has a predetermined relationship between a default standard deviation of the motion strength and an exercise intensity scale. The exercise intensity calculator collects a time series data of the motion strengths within a predetermined first time frame, obtains a standard deviation of thus collected motion strengths, and converting the standard deviation into an instant exercise intensity within the intensity scale in accordance with the predetermined relationship. The standard deviation with regard to the motion strengths can be well concordant with the exercise intensity, and therefore gives the accurate exercise intensity on a real-time basis.

15 Claims, 14 Drawing Sheets

U.S. PATENT DOCUMENTS

| | | | |
|---|---|---|---|
| RE35,598 E * | 9/1997 | Sadoff et al. ............. 73/379.01 |
| 5,690,582 A * | 11/1997 | Ulrich et al. .................... 482/4 |
| 5,807,267 A * | 9/1998 | Bryars et al. ................. 600/500 |
| 5,839,901 A * | 11/1998 | Karkanen .................... 434/127 |
| 5,890,128 A * | 3/1999 | Diaz et al. ....................... 705/2 |
| 5,890,995 A * | 4/1999 | Bobick et al. ................... 482/4 |
| 5,941,837 A * | 8/1999 | Amano et al. ............... 600/595 |
| 5,989,188 A * | 11/1999 | Birkhoelzer et al. ........ 600/300 |
| 6,018,677 A * | 1/2000 | Vidrine et al. .............. 600/520 |
| 6,032,108 A * | 2/2000 | Seiple et al. .................... 702/97 |
| 6,287,262 B1* | 9/2001 | Amano et al. ............... 600/500 |
| 6,389,894 B1* | 5/2002 | Calame ................... 73/379.01 |
| 6,506,152 B1 | 1/2003 | Lackey et al. |
| 6,515,593 B1* | 2/2003 | Stark et al. ............. 340/870.07 |
| 6,605,044 B2* | 8/2003 | Bimbaum ................... 600/500 |
| 6,671,736 B2* | 12/2003 | Virine et al. ................. 709/238 |
| 6,675,041 B2* | 1/2004 | Dickinson ................... 600/509 |
| 6,697,048 B2* | 2/2004 | Rosenberg et al. .......... 345/161 |
| 6,749,537 B1* | 6/2004 | Hickman ........................ 482/8 |
| 6,783,482 B2* | 8/2004 | Oglesby et al. ............... 482/54 |
| 6,790,178 B1* | 9/2004 | Mault et al. .................. 600/300 |
| 6,798,378 B1* | 9/2004 | Walters ................. 342/357.06 |
| 6,906,533 B1* | 6/2005 | Yoshida ....................... 324/692 |
| 6,921,351 B1* | 7/2005 | Hickman et al. ............... 482/8 |
| 6,950,695 B2* | 9/2005 | Chen ........................... 600/509 |
| 6,982,700 B2* | 1/2006 | Rosenberg et al. .......... 345/157 |
| 7,166,062 B1* | 1/2007 | Watterson et al. .............. 482/8 |
| 7,187,960 B2* | 3/2007 | Abreu ......................... 600/310 |
| 7,229,416 B2* | 6/2007 | Chen ........................... 600/500 |
| 7,232,416 B2* | 6/2007 | Czernicki ................... 600/595 |
| RE39,906 E * | 11/2007 | Roston et al. ............... 318/561 |
| 7,312,766 B1* | 12/2007 | Edwards ........................ 345/8 |
| 7,344,508 B2* | 3/2008 | Surina ......................... 600/587 |
| 7,359,624 B2* | 4/2008 | Adams et al. ............... 386/124 |
| 7,373,820 B1* | 5/2008 | James ........................... 73/488 |
| 7,762,952 B2* | 7/2010 | Lee et al. ..................... 600/300 |
| 2001/0020652 A1 | 9/2001 | Kadlubowski et al. |
| 2001/0020653 A1 | 9/2001 | Wilson et al. |
| 2001/0023902 A1 | 9/2001 | Wilson et al. |
| 2001/0038047 A1 | 11/2001 | Wilson et al. |
| 2003/0226695 A1 | 12/2003 | Mault |
| 2004/0102684 A1* | 5/2004 | Kawanishi et al. ........... 600/300 |
| 2004/0198554 A1* | 10/2004 | Orr et al. ........................ 482/8 |
| 2004/0220017 A1* | 11/2004 | Gordon et al. ................. 482/8 |
| 2004/0224822 A1* | 11/2004 | Verheem ......................... 482/8 |
| 2005/0107218 A1* | 5/2005 | Chuang et al. ................. 482/45 |
| 2005/0124463 A1* | 6/2005 | Yeo et al. ........................ 482/8 |
| 2005/0130802 A1* | 6/2005 | Kinnunen et al. ............... 482/8 |
| 2005/0164857 A1* | 7/2005 | Black .......................... 482/148 |
| 2005/0197237 A1* | 9/2005 | Chen .............................. 482/8 |
| 2005/0209050 A1* | 9/2005 | Bartels ........................... 482/8 |
| 2005/0209051 A1* | 9/2005 | Santomassimo et al. ........ 482/8 |
| 2005/0233859 A1* | 10/2005 | Takai et al. ..................... 482/3 |
| 2005/0233861 A1* | 10/2005 | Hickman et al. ............... 482/8 |
| 2005/0272564 A1* | 12/2005 | Pyles et al. .................... 482/54 |
| 2006/0020177 A1* | 1/2006 | Seo et al. ..................... 600/300 |
| 2006/0052727 A1* | 3/2006 | Palestrant ................... 600/595 |
| 2006/0063644 A1* | 3/2006 | Yang ............................. 482/4 |
| 2006/0084851 A1* | 4/2006 | Lee et al. ..................... 600/301 |
| 2006/0098772 A1* | 5/2006 | Reho et al. ................. 377/24.2 |
| 2006/0183602 A1* | 8/2006 | Astilean ......................... 482/7 |
| 2006/0183603 A1* | 8/2006 | Astilean ......................... 482/8 |
| 2006/0189437 A1* | 8/2006 | Cohen et al. ................... 482/7 |
| 2006/0229163 A1* | 10/2006 | Waters ........................... 482/8 |
| 2007/0021269 A1* | 1/2007 | Shum ............................ 482/8 |
| 2007/0033068 A1* | 2/2007 | Rao et al. ....................... 705/2 |
| 2007/0033069 A1* | 2/2007 | Rao et al. ....................... 705/2 |
| 2007/0051369 A1* | 3/2007 | Choi et al. ............. 128/204.21 |
| 2007/0142177 A1* | 6/2007 | Simms et al. .................. 482/8 |
| 2007/0173377 A1* | 7/2007 | Jamsen et al. .................. 482/8 |
| 2009/0240461 A1* | 9/2009 | Makino et al. ............. 702/141 |

FOREIGN PATENT DOCUMENTS

| | | |
|---|---|---|
| EP | 1 302 162 A2 | 4/2003 |
| EP | 1 366 712 A1 | 12/2003 |
| JP | 10-318779 A1 | 12/1998 |
| WO | WO-01/52718 A2 | 7/2001 |

OTHER PUBLICATIONS

Peter H. Veltink, et al., "Detection of Static and Dynamic Activities Using Uniaxial Accelerometers", IEEE Transactions on Rehabilitation Engineering, IEEE Inc. New York, U.S., vol. 4, No. 4, Dec. 1996, pp. 375-385, XP002315239, ISSN: 1063-6528.

Notification of Reasons for Refusal for the Application No. 2005-018679 from Japan Patent Office mailed Oct. 13, 2009.

Hara, Y. et al., "New Evaluation Method of the Physical Activity by an Acceleration Sensor",Engineering in Medicine and Biology Society, 2003, Proceedings of the 25th Annual international Conference of the IEEE EMBS, 2003, vol. 2 pp. 1712-1715.

Aminian, K. at al., "Physical Activity Monitoring Based on Accelerometry: Validation and Comparison with Video Observation", Medical and Biological Engineering and Computing, 1999, vol. 37, No. 2, pp. 304-308.

* cited by examiner

Table 82

| time (second) | α | β |
|---|---|---|
| 10 | 6.11 | 1.00 |
| 60 | 6.10 | 0.80 |

FIG. 20B

Table 83

| date | consumed energy | number of steps | activity level | > 1.1 METs | >1.5 METs | >2.0 METs | >2.5 METs | >3.0 METs | >3.5 METs | > 4.0 METs | > 5.0 METs | > 6.0 METs |
|---|---|---|---|---|---|---|---|---|---|---|---|---|
| 2004/9/7 | 28 | 145 | 1.02 | 16 | 11 | 8 | 6 | 4 | 4 | 4 | 1 | 0 |
| 2004/9/8 | 84 | 1200 | 1.06 | 86 | 62 | 30 | 4 | 1 | 0 | 0 | 0 | 0 |
| 2004/9/9 | 500 | 5720 | 1.37 | 401 | 207 | 112 | 71 | 50 | 36 | 26 | 20 | 11 |
| 2004/9/10 | 713 | 11443 | 1.53 | 540 | 289 | 190 | 127 | 82 | 57 | 40 | 20 | 3 |
| 2004/9/11 | 1365 | 24372 | 2.02 | 770 | 576 | 436 | 316 | 209 | 143 | 77 | 24 | 4 |
| 2004/9/12 | 831 | 12050 | 1.62 | 554 | 366 | 264 | 170 | 111 | 56 | 35 | 6 | 4 |
| 2004/9/13 | 690 | 10946 | 1.52 | 516 | 258 | 166 | 116 | 80 | 59 | 47 | 33 | 8 |
| 2004/9/14 | 788 | 10909 | 1.59 | 639 | 339 | 200 | 124 | 75 | 47 | 35 | 24 | 7 |
| 2004/9/15 | 624 | 10539 | 1.47 | 509 | 263 | 175 | 111 | 75 | 39 | 27 | 6 | 0 |
| 2004/9/16 | 684 | 9670 | 1.51 | 562 | 282 | 173 | 106 | 65 | 41 | 33 | 18 | 8 |
| 2004/9/17 | 879 | 14542 | 1.66 | 615 | 345 | 238 | 156 | 101 | 72 | 62 | 34 | 8 |
| 2004/9/18 | 730 | 9425 | 1.55 | 545 | 332 | 231 | 140 | 70 | 46 | 30 | 6 | 0 |
| 2004/9/19 | 556 | 9112 | 1.42 | 459 | 262 | 171 | 103 | 50 | 27 | 13 | 2 | 0 |
| 2004/9/20 | 692 | 5660 | 1.52 | 594 | 344 | 223 | 115 | 56 | 23 | 7 | 0 | 0 |
| 2004/9/21 | 524 | 10657 | 1.39 | 336 | 189 | 139 | 97 | 75 | 62 | 47 | 21 | 3 |
| 2004/9/22 | 116 | 3910 | 1.09 | 63 | 46 | 37 | 32 | 23 | 13 | 5 | 1 | 0 |
| 2004/9/23 | 4 | 0 | 1 | 4 | 3 | 1 | 0 | 0 | 0 | 0 | 0 | 0 |
| 2004/9/24 | ... | ... | ... | ... | ... | ... | ... | ... | ... | ... | ... | ... |
| 2004/9/25 | ... | ... | ... | ... | ... | ... | ... | ... | ... | ... | ... | ... |

PHYSICAL ACTIVITY MEASURING SYSTEM

TECHNICAL FIELD

The present invention is directed to a physical activity measuring system, and more particularly to such a self-contained portable system which is carried by a user to give a real-time exercise intensity for body motions of a user.

BACKGROUND ART

Japanese Patent Publication JP10-318779 discloses an exercise intensity level storing device which utilizes a body sensor which provides an electric signal indicative of the body motions of the user. In order to determine the exercise intensity, the device includes a processor that converts the body motions into the number of steps taken to give a combination of the amplitude of the electric signal and the number of steps. Then, the processor refers to a relation already obtained between the combination and an exercise intensity scale to obtain therefrom one of the exercise intensities in the scale as corresponding to the combination. Unfortunately, the above scheme is found not satisfactory in giving an accurate exercise intensity truly indicative of the body motions taken by the user.

DISCLOSURE OF THE INVENTION

In view of the above insufficiency, the present invention has been achieved to provide a physical activity measuring system which is capable of analyzing body motions of a user to determine the exercise intensity as accurate as possible. The system in accordance with the present invention includes a portable device which is adapted to be carried by the user and is equipped with a body sensor and an indicator for indication of the exercise intensity. The body sensor is configured to sense body motions of the user to give corresponding motion strength. The portable device includes a processor configured to constitute an exercise calculator which has a predetermined relationship between a default standard deviation of the motion strength and an exercise intensity scale. The exercise intensity calculator collects a time series data of the motion strengths within a predetermined first time frame, obtains a first standard deviation of thus collected motion strengths, and converting the first standard deviation into an instant exercise intensity within the intensity scale in accordance with the predetermined relationship. The standard deviation with regard to the motion strengths can be well concordant with the exercise intensity, and therefore gives the accurate exercise intensity on a real-time basis.

Preferably, the exercise intensity calculator is configured to collect another time series data of the motion strengths during each successive one of second time frames each being equal or greater than the first time frame so as to obtain a second standard deviation of thus collected motion strengths for each second time frame. Then, the second standard deviation for each second frame is converted into a normal exercise intensity within the scale also in accordance with the predetermined relationship. The processor is also configured to constitute an exercise analyzer which analyzes a record set of the normal exercise intensities in order to obtain a sum of the second time frames with regard to each of the normal exercise intensities assigned to the second time frame. Thereafter, the exercise analyzer provides a data set in which each of the normal exercise intensities is associated with the sum of the second time frame. In this instance, the indicator is provided in the form of a display for presenting the data set in addition to the instant exercise intensity. Thus, the user can be easy to acknowledge the amount of one's own physical exercise in terms of the exercise intensity and the accumulated time for that exercise.

The display may be designed to present the data set in such a format that all of the normal exercise intensities are associated respectively with the sums of the corresponding second time frames for easy confirmation of the exercise result by the user.

The system may be provided with a memory configured to give a history data table which stores the data set on a daily basis. In this connection, the system includes a pager which is configured to retrieve the data set for a selected date from the history memory for presenting the retrieved data set on the display. Thus, the user can refer to the history of the exercise for reviewing the data on the selected date.

Further, the processor is preferred to constitute an aerobic exercise analyzer which has a predetermined intensity threshold representing an aerobic threshold. The aerobic exercise analyzer compares the normal exercise intensity with the intensity threshold so as to increment a time count when the normal exercise intensity exceeds the intensity threshold, and issues an achievement signal when the time count exceeds a predetermined time threshold. The indicator is configured to give an indication of such condition, in response to the achievement signal. Thus, the system can inform the user of the aerobic exercise condition as soon as the user's exercise goes into the aerobic condition, thereby assisting the improvement of the user's exercise.

The aerobic exercise analyzer may be configured to compare the normal exercise intensity with the intensity threshold so as to obtain a sum of the second time frames in each of which the normal exercise intensity exceeds the intensity threshold. In this instance, the indicator is configured to present the sum in association with the intensity threshold, thereby notifying the user of the amount of the aerobic exercise in terms of the time period.

In order to give a time-dependent statistic with regard to the aerobic exercise for easy review by the user, the aerobic exercise analyzer may be designed to compare at least one of the normal exercise intensity and the instant exercise intensity with the intensity threshold so as to increment a time count until at least one of the normal exercise intensity and the instant exercise intensity falls below the intensity threshold within each of time zones of the day. The time count is stored as related to each of the associated time zones such that the display presents the time count per each time zone. Accordingly, the amount of the aerobic exercise can be shown in association with the time zones of the day.

The intensity threshold can be preset or varied in consideration of the user's physical characteristics. In addition, it is mostly preferred that the aerobic exercise analyzer is configured to allow the user to designate a current one of the instant exercise intensity and the normal exercise intensity as the intensity threshold. Thus, the system can be easily customized in well reflective of the user's own physical capability.

Further, the processor may be configured to constitute a BMR calculator which processes physical data of the user for obtaining a basal metabolic rate [BMR] inherent to the user; and a caloric consumption calculator which obtains a caloric consumption which is a function of the normal exercise intensity, the basal metabolic rate [BMR], and also current time of the day. Thus, the caloric consumption calculator can give the caloric consumption resulting from the user's exercise taken by the current time of the day. In this connection, the display is configured to present thus obtained caloric consumption for easy review by the user.

The caloric consumption calculator may be also configured to provide the caloric consumption for each of time zones of the day such that the display presents the caloric consumption in association with each of the time zones, thereby giving a statistic of caloric consumption on a time-zone basis within the day.

The system may additional includes food data input means configured to input food data taken by the user, and a calorie intake calculator configured to process the food data input by the current time of the day to give an accumulated caloric intake. In this instance, the caloric consumption calculator is designed to obtain a current caloric consumption which is a function of the normal exercise intensity made by the current time of the day and the basal metabolic rate of the user. A caloric balance calculator is also included to give a current caloric balance which is the above accumulated caloric intake minus the current caloric consumption. The system further includes a living pattern analyzer and a living pattern reader. The living pattern analyzer has a plurality of standard living patterns each of which defines a standard exercise intensity for each of time zones of the day. The living pattern analyzer analyzes the normal exercise intensity per each of the time zones in comparison with the standard living patterns so as to designate one of the standard living patterns as a specific living pattern for the user. The living pattern reader operates to read the current time of the day, and refer to the specific living pattern so as to retrieve therefrom the standard exercise intensity and designate it as an estimated exercise intensity with regard to each of the time zones for the rest of the day. Also included in the system is a caloric consumption estimator which gives a forthcoming caloric consumption necessary to make the estimated exercise intensities for the rest of the day, and therefore determines a forthcoming caloric balance which is the forthcoming caloric consumption minus the current caloric balance. Based upon the forthcoming caloric balance, an advice generator generates an advice message reflecting the forthcoming caloric balance for presenting the advice message on the display. With this arrangement, the system can give an optimum schedule to the user with regard to the caloric intake of the foods or the caloric consumption by the physical exercise in compensation for the forthcoming caloric balance.

In order to make the portable device a self-contained, yet realizes the above advantageous functions, the processor of the portable device is preferred to constitute the BMR calculator, the caloric intake calculator, the caloric balance calculator, the living pattern analyzer, the living pattern reader, the caloric consumption estimator, and the advise generator.

Alternatively, the system may be composed of the portable device and a workstation which is provided separately from the portable device and is designed to communicate therewith. In this instance, it is preferred that the processor of the portable device is configured to realize the BMR calculator; the calorie intake calculator, the caloric consumption calculator, the caloric balance calculator, and additionally include a communication interface for transmitting the normal exercise intensity as well as the current caloric balance to the workstation. While on the other hand, the workstation is configured to have the living pattern analyzer, the living pattern reader, the caloric consumption estimator; and the advise generator, in addition to a communication interface and a system clock recording a current date and time. In this instance, the advice generator transmits the advice message through the communication interfaces for presenting the message on the display of the portable device. With such functional sharing, the portable device can be made compact, yet enjoying sophisticated and beneficial analytical results of the exercise.

The workstation is preferably equipped with a monitor, a data storage giving a data table which stores the normal exercise intensities for each of the time zones over a plurality of days, a term designator which designates a term defined by a start date and an end date, and a daily activity analyzer. The daily activity analyzer selects one of the time zones, and determines, based upon the exercise intensity, an activity level for the selected time zone with regard to each day included in the designated term. Then, the daily activity analyzer obtains a tendency of the activity level over the designated term, generates a living rhythm message indicating thus obtained tendency, and issues the tendency message to be displayed on the workstation display. This is advantageous for the user to recognize and maintain one's own living rhythms by taking care of foods and physical exercise schedule.

In order to obtain the tendency of the activity level, the daily activity analyzer collects the general exercise intensities of the selected time zone for the dates included in the term, and defines a reference exercise intensity as an average of the collected general exercise intensities over the designated term. Then, the daily activity analyzer compares the general exercise intensity of the selected time zone for each of the dates within the term with the reference exercise intensity to obtain divergence therebetween on a daily basis, thereby determining one of the activity levels as corresponding to thus obtained divergence and generating the tendency in terms of thus determined activity level.

The daily activity analyzer is preferred to generate a first living rhythm message when the tendency indicates no substantial change in the activity level, a second living rhythm message when the tendency indicates an incline of the activity level, and a third message when the tendency indicates a decline of the activity level. These living rhythm messages are different from each other to give helpful information to the user.

These and still other advantageous features of the present invention will become more apparent from the following description of the preferred embodiments when taken in conjunction with the attached drawings.

BRIEF DESCRIPTION OF THE DRAWINGS

FIGS. 12A, 12B, and 12C are graphs respectively illustrating exercise intensity ratio for persons of different living patterns;

FIGS. 20A and 20B show an example of the acceleration-exercise intensity relation table 82 and history data table 83.

BEST MODE FOR CARRYING OUT THE INVENTION

Figure 1:
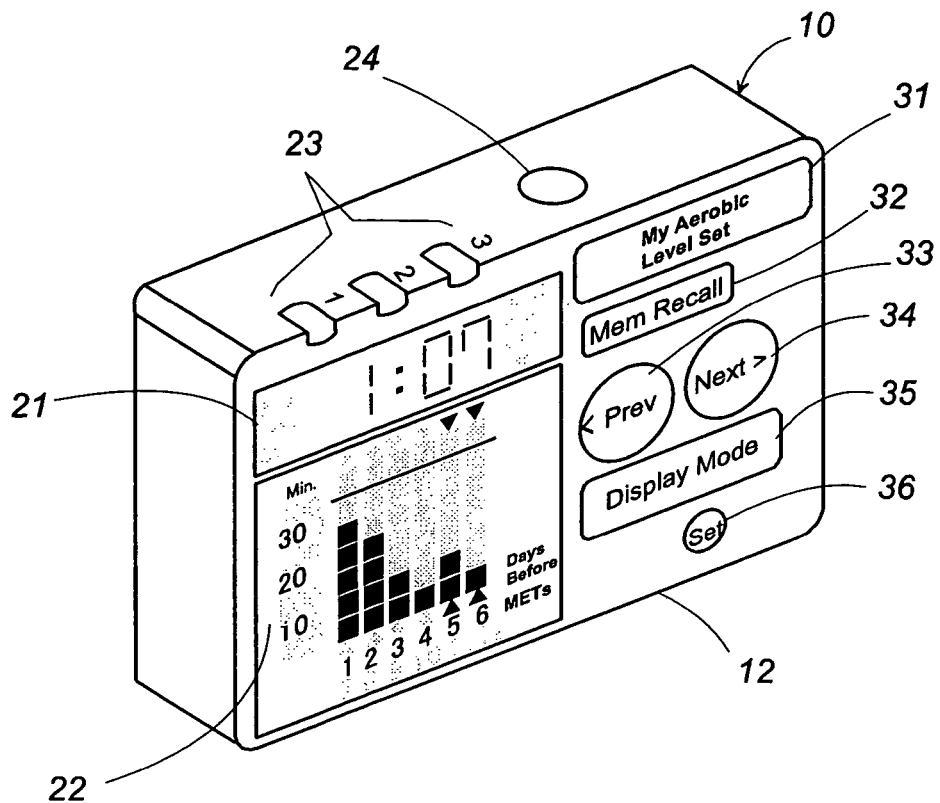
FIG. 1 is a perspective view of a portable device constituting a physical activity measuring system in accordance with a preferred embodiment of the present invention.
Figure 4:
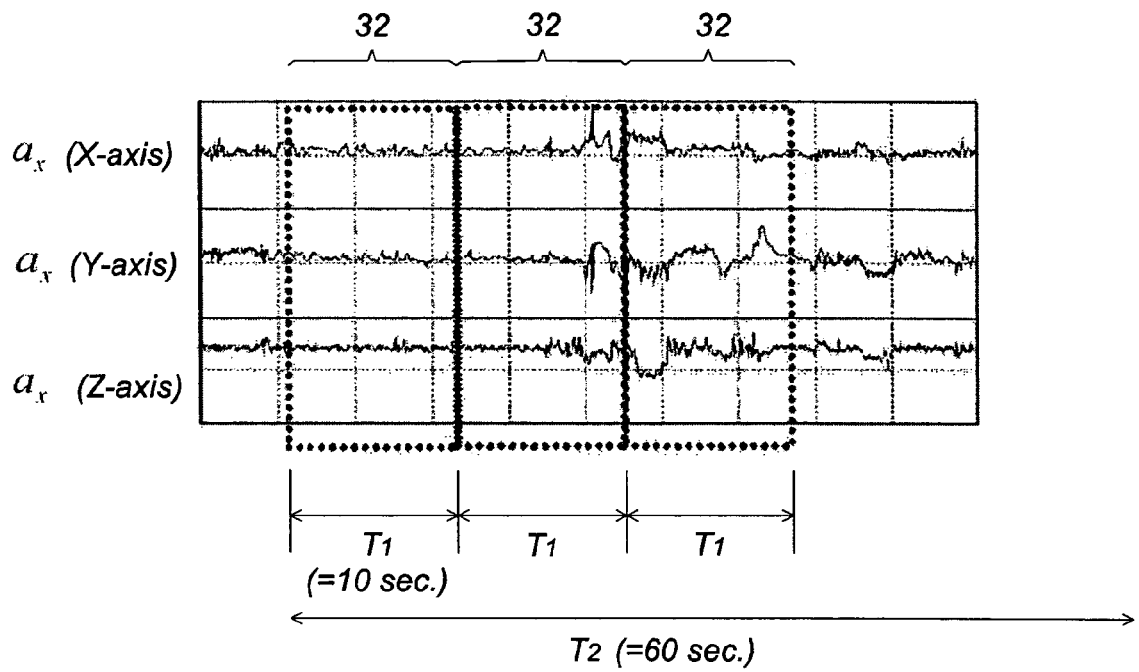
FIG. 4 is a graph illustrating acceleration signals to be processed in the device as indicative of body motions of a user.

Referring now to FIG. 1, there is shown a portable device 10 constituting a physical activity measuring system in accordance with a preferred embodiment of the present invention. The portable device 10 is designed to be carried by a user, and includes a housing 12 incorporating a body sensor 50 for sensing body motions of the user. The housing 12 further includes an indicator or display 20 composed of an upper window 21, a lower window 22, a level indicator 23, and a lamp 24. Buttons 31 to 36 are also provided on front of the housing 12 to realize input means for entry of data by the user, and also switches for performing several functions of the device, as will be discussed later. The body sensor is realized by a three-axis acceleration sensor 50 which generates acceleration signals in all three directions, namely, $a_x$, $a_y$, and $a_z$ in x-axis, y-axis, and z-axis, as shown in FIG. 4.

Figure 3:
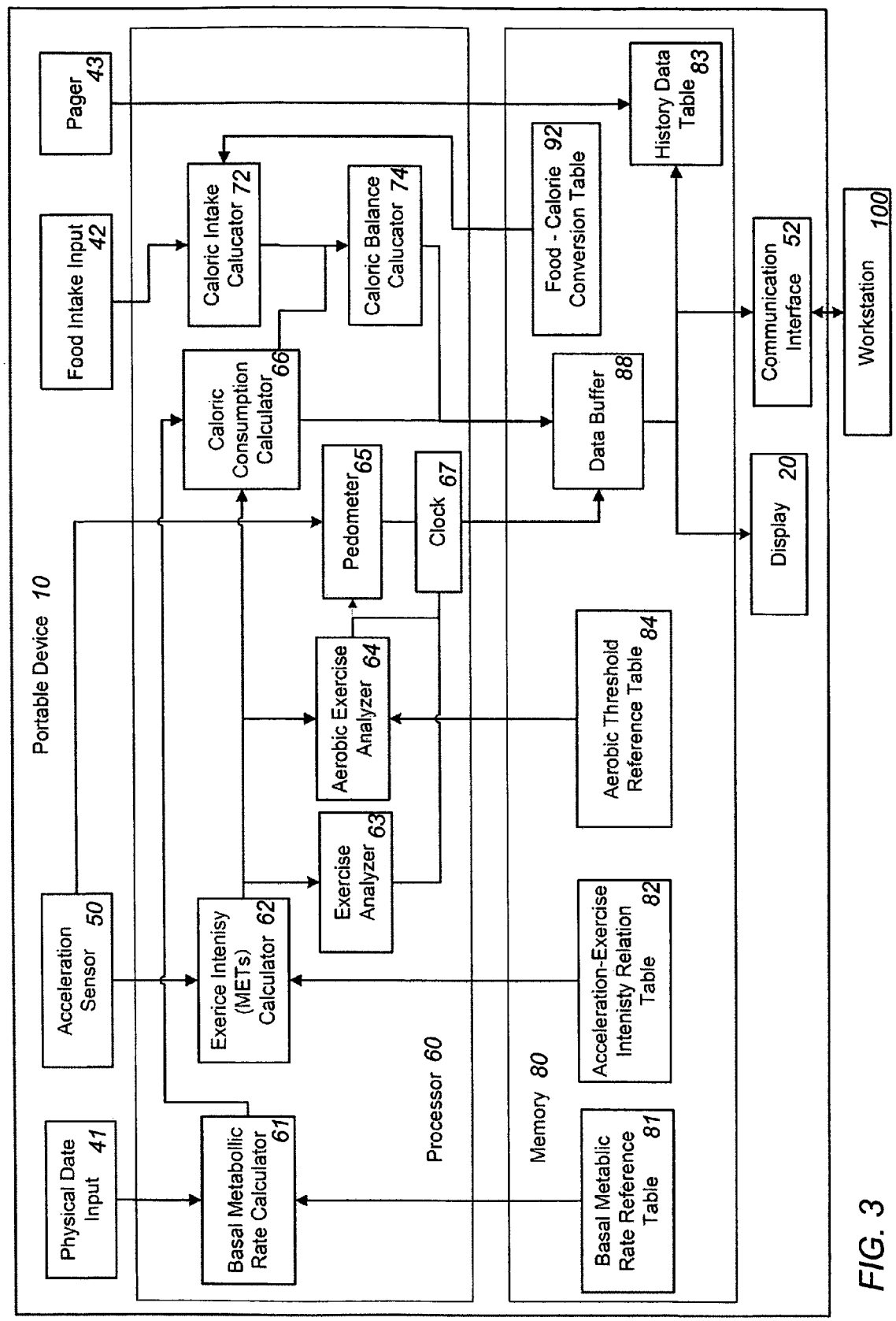
FIG. 3 is a block diagram illustrating a functional arrangement of the device.
Figure 5:
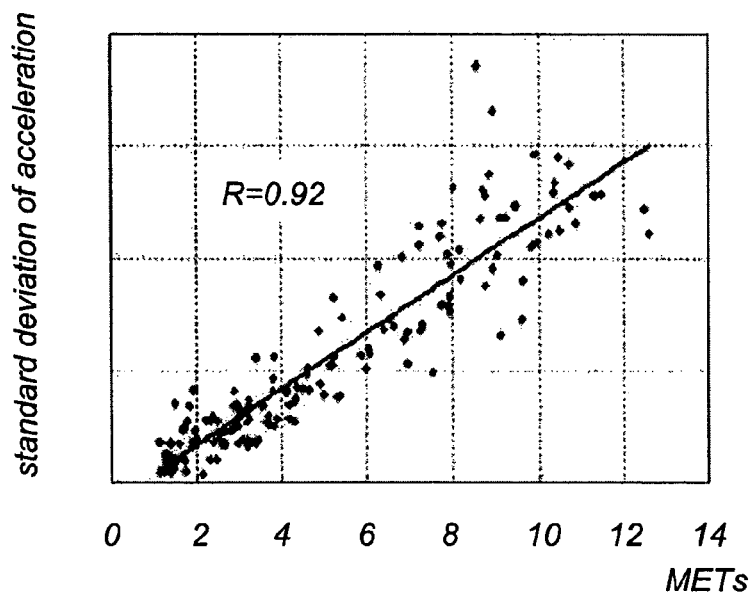
FIG. 5 is a graph illustrating a relation between a standard deviation of the acceleration signal and exercise intensity.

Also incorporated in the housing 12 is a microprocessor or processor 60 responsible for performing the functions, and a memory 80 for storing necessary data referred to by the processor 60 as well as results provided by the processor 60. As shown in FIG. 3, the processor 60 constitutes an exercise intensity calculator 62 which analyzes the acceleration signals to determine an equivalent exercise intensity in terms of metabolism [METs] by referring to an acceleration-exercise intensity relation table 82 (an example of which is shown in FIG. 20A) stored in the memory 80. The table 82 contains parameters ($\alpha$) and ($\beta$) which determines the exercise intensity (K) in accordance with the following equation:

$$K = \alpha \cdot Sw + \beta$$

Wherein Sw is a standard deviation of the accelerations $a_x$, $a_y$, and $a_z$. That is, the exercise intensity calculator 60 converts the standard deviation (Sw) into the corresponding exercise intensity (K) based upon a predetermined relation obtained between the standard deviation (Sw) of the accelerations and the exercise intensity, as shown in FIG. 5. The figure provides a linear equation expressed by Sw=a·K+b, which is obtained by a least square method at a correlation coefficient of R=0.92. Thus, given the standard deviations (Sw) of the accelerations, the exercise intensity can be determined with reference to parameters ($\alpha$) and ($\beta$) in the table 82. The standard deviation (Sw) of the accelerations is obtained by the following equations:

$$Sw(i) = \sqrt{\left\{ \frac{\sum ((a_{xk} - b_{x(i)})^2 + (a_{yk} - b_{y(i)})^2 + (a_{zk} - b_{y(i)})^2)}{n-1} \right\}} \quad (2)$$

$$b_{x(i)} = \left( \frac{\sum a_{xk}}{n} \right) \quad (3)$$

$$b_{y(i)} = \left( \frac{\sum a_{yk}}{n} \right) \quad (4)$$

$$b_{z(i)} = \left( \frac{\sum a_{zk}}{n} \right) \quad (5)$$

in which $a_{yk}$, and $a_{zk}$ are respectively k-th accelerations, respectively for x-, y-, z-axes, (n) is a sampling number, and (i) is an integer indicative a time period for sampling the accelerations.

The equations (3), (4), and (5) represent the average of the accelerations after elapse of the time defined by the integer (i). In this embodiment, the accelerations are sampled 1182 times per one minute, i.e., 19.7 times per one second.

Figure 2:
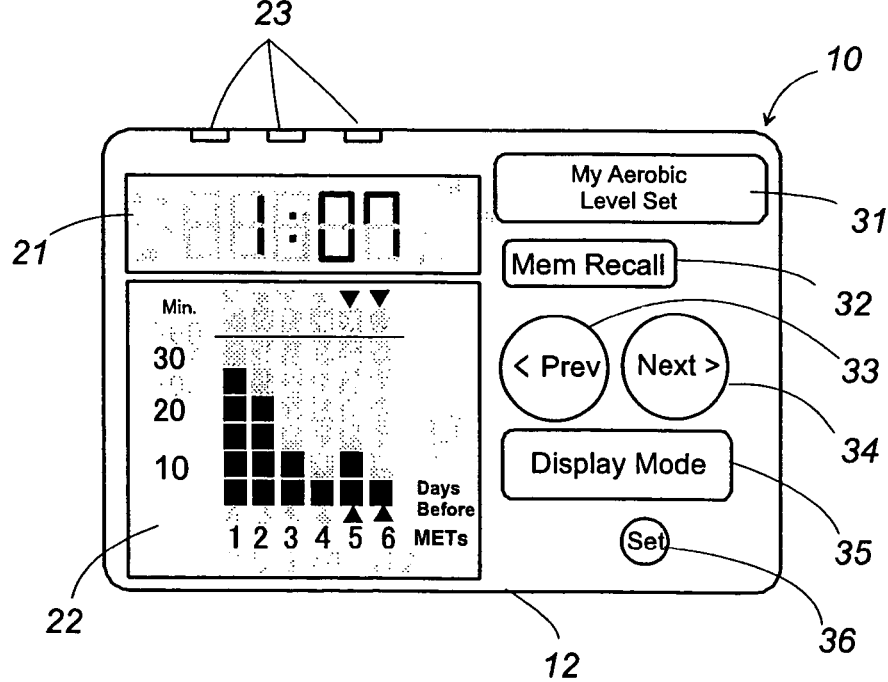
FIG. 2 is a front view of the device.

It is noted in this connection that the exercise intensity calculator 62 is designed to calculate an instant exercise intensity (K1) within a first time frame (T1), for example, 10 seconds, as well as to calculate a general exercise intensity (K2) over a second time frame (T2), for example, 60 seconds, as shown in FIG. 2. In this consequence, the average accelerations may vary with varying time period from (T1) to (T2), which results in varying standard deviations (Sw) and therefore varying parameters ($\alpha$) and ($\beta$). In compensation for possible variations in the average accelerations, the table 82 gives parameters ($\alpha$1), ($\beta$1) and ($\alpha$2), ($\beta$2) for determination of the instant exercise intensity (K1) and the general exercise intensity (K2), respectively from K1=$\alpha$1·Sw(T1)+$\beta$1 and K2=$\alpha$2·Sw(T2)+$\beta$2. In some case, $\alpha$1=$\alpha$2 and $\beta$1=$\beta$2 may be applicable.

Thus, the instant exercise intensity (K1) and the general exercise intensity (K2) are determined based respectively upon the standard deviation Sw(10) and Sw(60) obtained from the following equations (2-1) and (2-2).

$$Sw(10) = \sqrt{\left\{ \frac{\sum_{1}^{197} ((a_{xk} - b_{x(10)})^2 + (a_{yk} - b_{y(10)})^2 + (a_{zk} - b_{y(10)})^2)}{196} \right\}} \quad (2\text{-}1)$$

$$Sw(60) = \sqrt{\left\{ \frac{\sum_{1}^{1182} ((a_{xk} - b_{x(60)})^2 + (a_{yk} - b_{y(60)})^2 + (a_{zk} - b_{y(60)})^2)}{1181} \right\}} \quad (2\text{-}2)$$

Figures 6, 7A, 7B, 7C, 8A, 8B, 8C, 8D, 8E, 8F:
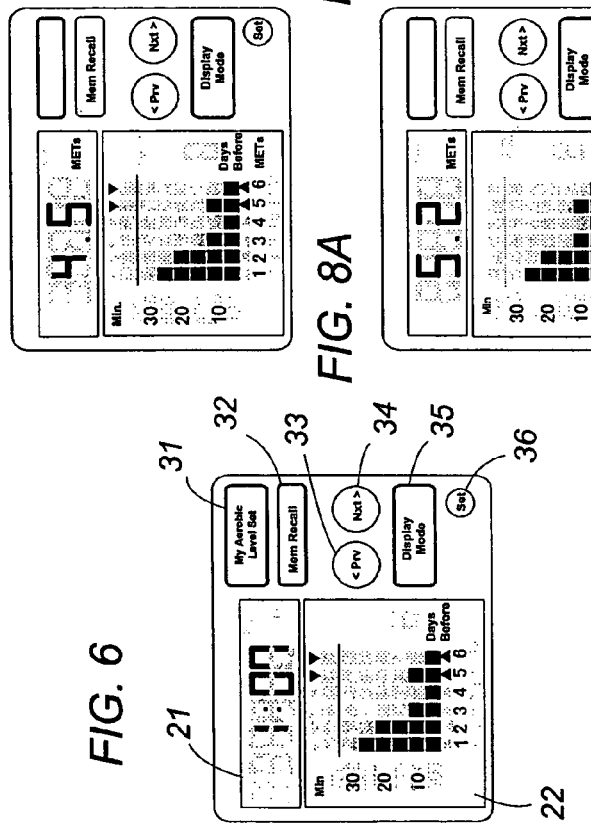
FIG. 6 is a front view illustrating a display pattern in an operation mode of the device.
FIGS. 7A, 7B, and 7C are front views respectively illustrating various display patterns in different operation modes of the device.
FIGS. 8A, 8B, 8C, 8D, 8E, and 8F are front views respectively illustrating various display patterns in different operation modes of the device.

The exercise intensity calculator 61 constantly updates the instant exercise intensities (K1) [METs] which is stored in a data buffer 88 to be presented in the upper window 21, as shown in FIG. 7A. Concurrently, the calculator 61 obtains the general exercise intensity (K2) every 60 seconds, i.e., the second time frame (T2). That is, the calculator 61 collects time series data of the accelerations during each successive second time frame (T2=60 seconds) to give the general exercise intensity every 60 seconds which is fed to an exercise analyzer 63 provided in the processor 60.

The exercise analyzer 63 analyzes a record set of the normal exercise intensities (K2) in order to give a statistical data in which each calculated general exercise intensity (K2) is associated with the total time, i.e., the sum of the corresponding second time frames, providing a resulting data set which is stored in a data buffer 88 such that the data set is presented in the lower window 22 in a graphical format, as shown in FIG. 7A. The exercise analyzer 63 operates to accumulate the data set for 24 hours of the day and is reset at 0:00.

Although the second time frame (T2) is set to be larger than the first time frame (T1) in this embodiment, the second time frame (T2) may be set to be equal to the first time frame (T1). It is noted here that the data set is also recorded together with a current date and time provided by a clock 67, and is transferred from the data buffer 88 into a history data table 83 (an example of which is shown in FIG. 20B) having a capacity of keeping the data set covering several days or weeks. The history data table 83 is referred to by a pager 43 to give the data set of the previous date selected at the pager for display in the tower window 22.

The processor 60 is also configured to constitute an aerobic exercise analyzer 64 which compares the normal exercise intensity (K2) with a predetermined intensity threshold (Kt) per each second time frame (T2) to judge whether an aerobic exercise condition for the user is reached by the user's body motions. The intensity threshold (Kt) is provided in an aerobic threshold reference table 84, the contents of which are shown in table below. The table classifies the intensity threshold (Kt) according to the exercise level (I, II, III, IV), sex, and age. Thus, upon designation of these parameters by the user, the aerobic exercise analyzer 64 retrieves the corresponding intensity threshold (Kt) from the table 84 as a basis for comparison with the general exercise intensity (K2) being obtained. The intensity threshold (Kt) thus retrieved is displayed in the upper window 21 of the device upon being called, as shown in FIG. 7B and FIGS. 8A and 8B. Also, the analyzer 64 is configured to give a pointer (marked by a triangle in these figures) indicating the intensity threshold (Kt) adjacent to an exercise intensity scale appearing in the bottom of the lower window 22.

|  |  | Age | | | | |
| --- | --- | --- | --- | --- | --- | --- |
| Level | Sex | 20 - | 30 - | 40 - | 50 - | 60 - |
| I | Male | 5.1 | 4.8 | 4.5 | 4.2 | 4.1 |
|  | Female | 4.4 | 4.2 | 4.1 | 4.0 | 3.8 |
| II | Male | 5.8 | 5.7 | 5.5 | 5.3 | 5.0 |
|  | Female | 5.0 | 4.8 | 4.7 | 4.5 | 4.4 |
| III | Male | 6.2 | 6.0 | 5.7 | 5.4 | 5.2 |
|  | Female | 5.5 | 5.2 | 5.0 | 4.7 | 4.4 |
| IV | Male | 7.0 | 7.0 | 7.0 | 7.0 | 7.0 |
|  | Female | 6.0 | 6.0 | 6.0 | 6.0 | 6.0 |

The aerobic exercise analyzer 64 provides two analysis modes, i.e., a first analysis mode for giving the total time of the aerobic condition achieved by the current time of the day as well as giving how long the aerobic condition continues, and a second analysis mode for giving the time of the aerobic condition achieved by the current time of the day with regard to each of time zones, for example, each hour of the day.

In the first analysis mode, the analyzer 64 obtains a sum of the number of the second time frames (T2) in each of which the normal exercise intensity (K2) exceeds the intensity threshold (K2>Kt), and provides the total time of the aerobic condition achieved by the current time of the day which is displayed together with the intensity threshold (Kt), as shown in FIGS. 7B and 7C. In this instance, the intensity threshold (Kt=5.2 METs) and the total time of 20 minutes are indicated respectively as a numeric value in the upper window 21 and as a graphical representation in the lower window 22 of FIG. 7B, while the total time of 20 minutes is indicated as a numerical value in the upper window 21 of FIG. 7C. Switching of the display mode between FIGS. 7B and 7C is made by pressing the arrowed buttons 33 and 34. Also, the analyzer 64 increments a time count each time the normal exercise intensity (K2) exceeds the intensity threshold (Kt), and continues incrementing the time count until the exercise intensity (K2) falls below the threshold (Kt). The time count thus indicating how long the aerobic condition continues is compared with predetermined time thresholds, i.e., 10, 20, and 30 minutes in order to notify the amount of the aerobic condition in terms of the number of times that the aerobic condition continues through 10 minutes. That is, when the aerobic condition continues through 10 minutes, the analyzer 64 gives a resulting signal to highlight a first level "1" in the level indicator 23, as shown in FIG. 1. Similarly, second level "2" and third level "3" of the indicator 23 are highlighted upon seeing that the aerobic condition further continues through 20 minutes and 30 minutes, respectively. Thus, the user can be informed of the aerobic conditions being made on a real time basis. In addition, once the aerobic condition is acknowledged, the analyzer 64 issues a resulting signal to highlight the lamp 24 and keep it on until the aerobic condition disappears.

It is noted in this connection that the instant exercise intensity (K1) may be utilized together to give the time count, i.e., the time duration in which the aerobic condition continues. In this instance, the analyzer 64 is configured to set the time count as corresponding to the second time frame (T2=1 minute) when the general exercise intensity (K2) first exceeds the threshold (Kt), and increment the time count until the instant exercise intensity (K1) falls below a lowered threshold Ktt (=0.9×Kt). Upon seeing that the instant exercise intensity (K1) falls below the threshold (Ktt), the analyzer 64 resets the time count to zero. This scheme may give a more consistent evaluation of the aerobic condition.

In the second analysis mode, the analyzer 64 obtains a sum of the second time frames (T2) in each of which the normal exercise intensity (K2) exceeds the intensity threshold (K2>Kt), and gives a data set of the sum of the second time frames per each of time zones of the day, for example, per hour. The data set is constantly updated to give the data obtained by the current time of the day, and is represented in the lower window 22 such that the total time of the aerobic condition per each time zone, i.e., each hour of the day is represented in a graphical format, as shown in FIGS. 8A and 8B. The data set is stored in the history data table 83 as being related with the date and time so as to be reviewed later by the pager 43.

The aerobic exercise analyzer 64 is also configured to give a function of setting the intensity threshold, i.e., to designate a current one of the instant exercise intensity (K1) and the general exercise intensity (K2) as the intensity threshold (Kt) which overrides the one retrieved from the aerobic threshold reference table 84. That is, when the "My Aerobic Level Set" button 31 is kept pressed for one second or more, the current exercise intensity (K1) or (K2) is designated as a new intensity threshold (Kt). With this scheme, the device can be well customized for the user.

Figure 9:
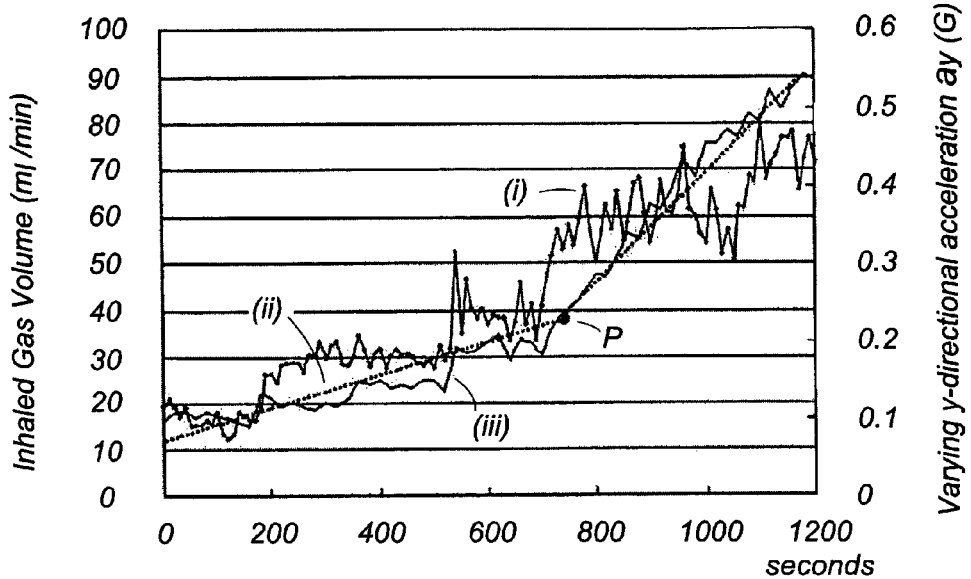
FIGS. 9 and 10 are graphs illustrating the relation between the anaerobic threshold and the varying acceleration in y-axis, respectively obtained for persons of difference exercise capabilities.
Figure 10:
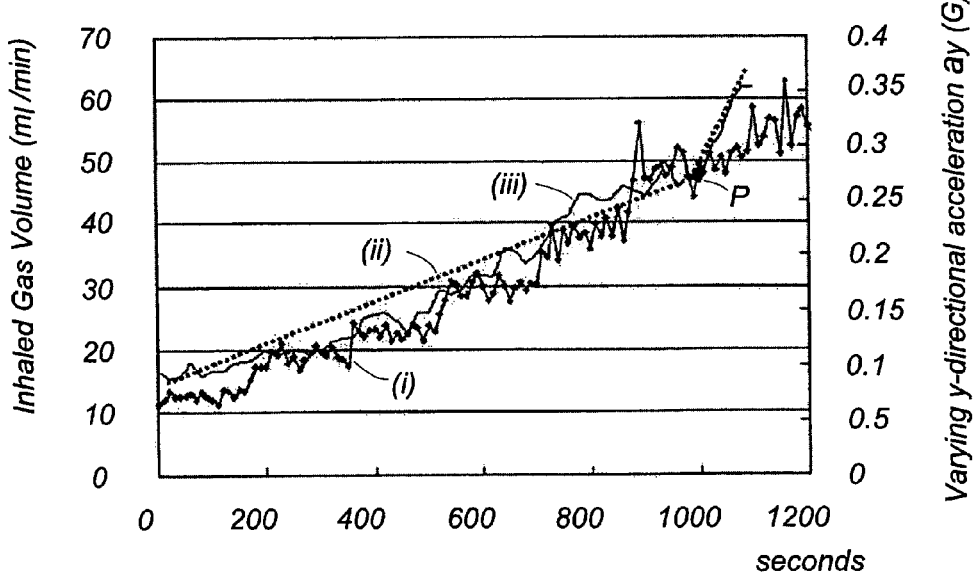

Alternatively, the aerobic exercise analyzer 64 may be replaced by an anaerobic exercise analyzer which is configured to determine the intensity threshold (Kt) as an anaerobic threshold. The anaerobic threshold is a point where the anaerobic process or condition becomes more dominant, and is found to be in direct relation with varying accelerations $a_y$ in y-direction, as demonstrated in FIGS. 9 and 10 which plot the inhaled gas volume (i), an approximation curve (ii) of (i), and varying linear accelerations (iii) in y-direction respectively for persons of different exercise capabilities. In either case, the point (P) of the anaerobic threshold, i.e., the intensity threshold (Kt) is found to correspond to 0.25 G of the acceleration $a_y$ in y-direction. Thus, the anaerobic exercise analyzer can determine the intensity threshold (Kt) which is equal to the general exercise intensity (K2) obtained at the time acceleration $a_y$ reaches 0.25 G.

Turning back to FIG. 3, the processor 60 also realizes a pedometer 65 which analyzes the composite of accelerations $a_x$, $a_y$, and $a_z$ from the sensor 50 with reference to a step threshold (St) and counts one step when the following inequality (6) is satisfied.

$$a_x^2 + a_y^2 + a_z^2 > St \qquad (6)$$

in which (St) is set to be 1.2 when Kt<=4, otherwise 1.5.

The composite is sampled 5 times within one second, and 4 steps or less counted within an initial time period of 5 seconds is neglected. The number of thus counted steps made by the current time of the day is displayed in the upper window 21 of FIG. 8C. Further, the pedometer 65 counts the number of steps per each time zone, i.e., per hour to give a corresponding representation in a graphical format to be displayed in the lower window 22 of FIGS. 8C, 8D, 8E, and 8F. When the user selects a particular time zone, for example, 1:00 p.m. to 1:59 p.m. as indicated by a triangular pointer on an hourly scale appearing in the bottom of the lower window 22 (FIG. 8D), the pedometer 65 gives the number of steps, in this instance, "206" corresponding to the selected time zone, and displays the numerical value in the upper window 21. The record set of the number of steps obtained for each day is stored in the history data table 83 to be later reviewed by the pager 43.

Further, the processor 60 constitutes a caloric consumption calculator 66 as well as a basal metabolic rate calculator 61 in order to obtain a caloric consumption in consequence of the user's physical exercise achieved by the current time of the day. The caloric consumption is determined as a function of the normal exercise intensity already obtained and the basal metabolic rate inherent to the user.

The basal metabolic rate [BMR] calculator 61 receives physical data of age, sex, and weight (W) entered at a physical data input 41 of the device, and provides a basal metabolic rate [BMR] per day by referring to a basal metabolic rate reference table 81 stored in the memory 80. The table 81 contains parameters different to age, sex and weight (W) for calculation of the basal metabolic rate [BMR], as shown in the table below.

| Age | Male | Female |
|---|---|---|
| 6-8 | 34.3 × W + 247 | 32.5 × W + 224 |
| 9-11 | 29.4 × W + 277 | 26.9 × W + 267 |
| 12-14 | 24.2 × W + 324 | 22.9 × W + 302 |
| 15-17 | 20.9 × W + 363 | 19.7 × W + 289 |
| 18-29 | 18.6 × W + 347 | 18.3 × W + 272 |
| 30-49 | 17.3 × W + 336 | 16.8 × W + 263 |
| 50-69 | 16.7 × W + 301 | 34.3 × W + 247 |
| 70- | 34.3 × W + 247 | 16.1 × W + 224 |

The basal metabolic rate [BMR] retrieved from the table is converted in a corresponding metabolic index [BM] per minute (BM=BMR/1440) in match with the normal exercise intensity (K2).

The caloric consumption calculator 66 operates to first obtain an exercise caloric consumption (Ckm) according to the following equation (7):

$$Ckm = \frac{(K2 - 1) \cdot W}{60} \quad [\text{Kcal/min}] \qquad (7)$$

in which (W) is a weight of the user.

Then, the caloric consumption (Cm) per minute is determined as the exercise caloric consumption plus the metabolic index (Cm=Ckm+BM). The caloric consumption (Cm) thus obtained every one minute is stored in the data buffer 88 in association with the current date and time, and is processed to give a total caloric consumption by the current time of the day as well as to give a partial caloric consumption per each time zone. For example, the total caloric consumption of "306 kcal" is displayed in the upper window 21 (FIG. 8E), while the partial caloric consumption of "96 kcal" is displayed in the upper window 21 (FIG. 8F) for the time zone of 1:00 p.m. to 1:59 p.m. as indicated by a triangular pointer on an hourly scale appearing in the bottom of the lower window 22. In FIGS. 8E and 8F, the number of steps is displayed in a graphical format in the lower window 22 in relation to the time scale, and in correspondence to the caloric consumption. However, the caloric consumption per hour may be instead displayed in a like graphical format.

The various display modes as shown in FIGS. 7 and 8 can be selected by firstly pressing the "display mode" button 35 and then pressing the "PrV" button 34 or "Nxt" button 35. The "set" button 36 is provided for entry of the current date and time, while the "Mem Recall" button 32 is provided for activating the pager 43 to display the record with regard to the previous date selected.

Further, the device includes a food intake input 42 for entry of food data taken by the user, and the processor 60 is configured to constitute a caloric intake calculator 72 which processes the food data given by the current time of the day to calculate an accumulated caloric intake by reference to a food-calorie conversion table 92 in the memory 80. Thus, each time the food intake input 42 receives the amount and kind of the food, the caloric intake calculator 72 calculates an equivalent calorie and adds it to the previous calories, if any, thereby obtaining the accumulated caloric intake. In this connection, the processor 60 further constitutes a caloric balance calculator 74 which gives a current caloric balance as the accumulated caloric intake minus the current caloric consumption. Thus, both or either of the accumulated caloric intake and the current caloric balance is displayed on the upper window 21 upon requested, i.e., by pressing "display mode" button 35.

Figure 11:
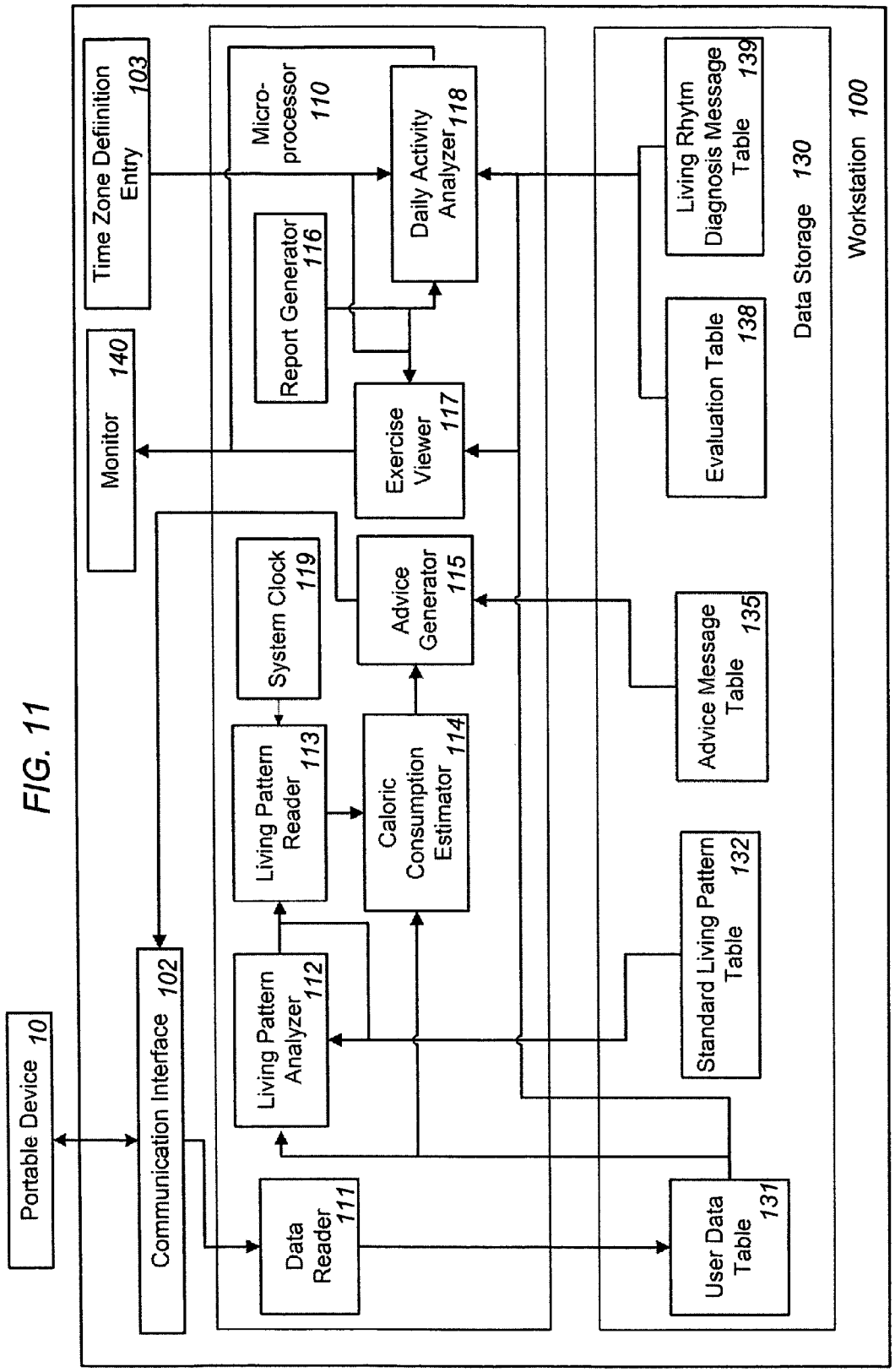
FIG. 11 is a block diagram illustrating a functional arrangement of a workstation which may be utilized in combination with the portable device.

In addition to the portable device having the above described functions, the system may utilize a workstation 100, i.e. a personal computer or server computer so as to make the best use of enhanced resources of the workstation, thereby providing more sophisticated analytical results or reports to the user. The device 10 and the workstation 100 include individual communication interfaces 52 and 102, respectively for intercommunication therebetween. In this instance, the device 10 is configured to transmit the data set of the normal exercise intensities (K2) as well as the current caloric balance to the workstation 100. As shown in FIG. 11, the workstation 100 includes a micro-processor 110, a data storage 130, an input means for entry of instructions, and a monitor 140, in addition to the communication interface 102.

Figure 12C:
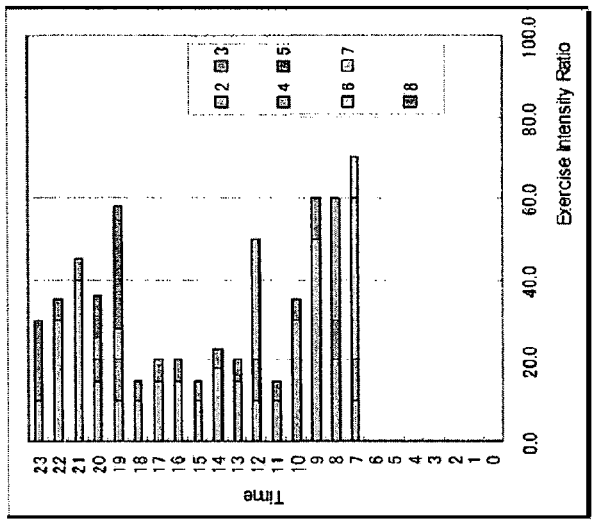
Figure 12C:
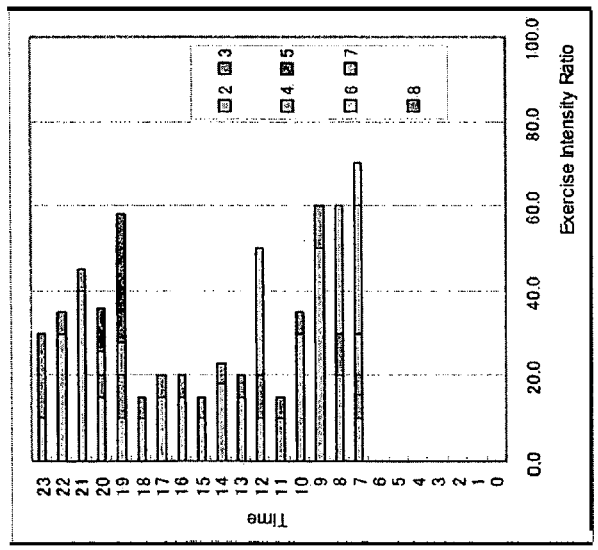

The micro-processor 110 is configured to provide a data reader 111 which reads the data set of the normal exercise intensities (K2) and the current caloric balance for storing them into a user data table 131 in the data storage 130. The user data table 131 is formatted to contain a personal code identifying the user and to store the general exercise intensities (K2) and the current caloric balance in association with the personal code. A living pattern analyzer 112 is realized in the micro-processor 110 to be given a plurality of different standard living patterns from a standard living pattern table 132 in the data storage 130. Each of different standard living patterns defines a standard exercise intensity for each of time zones within the day, i.e., for each hour in this instance, as shown in FIGS. 12A, 12B, and 12C. In these figures, an exercise intensity ratio is shown in a bar-graph format per one hour time zone. The exercise intensity ratio is determined as a ratio of the each intensity in terms of a time period relative to the total time for all exercise intensities. That is, each bar relating to each hour is divided into a plurality of time bands each representing the length of the time for making the corresponding exercise intensity. For this purpose, the general exercise intensities (K2) calculated at the device 10 are rounded off and classified into 8-grades. These figures are obtained for persons having different standard living patterns, for example, one for an office worker taking a train to work (FIG. 12A), another for an office worker taking a bicycle to work (FIG. 12B), and the rest for a full-time housewife (FIG. 12C).

The living pattern analyzer 112 collects the general exercise intensities (K2) transmitted from the device 10 over a wide range of the time zones within the day, and compares the resulting data with the standard living patterns in order to expect one of the standard living pattern as analogous to that given by the data, thereby designating thus found pattern as a specific living pattern for the user. For determining the specific living pattern, a consideration is made to a variance (V) defined by the following equation (8):

$$V = \sum (\Delta P)^2 - \frac{\left(\sum (\Delta P)^2\right)}{n} \quad (8)$$

in which ΔP=P1−P2, and P1 is a standard average of the exercise intensity ratio at each time zone for each of the standard living patterns, P2 is an average of the exercise intensity ratio at each corresponding time zone obtained with respect to the general exercise intensities (K2) of the user, and (n) is the number of the hours in each time zone. Then, the analyzer 112 selects one of the standard living patterns giving a minimum variance (V) and expects it to be the specific living pattern. Based upon thus expected specific living pattern, a living pattern reader 113 also provided by the micro-processor 110 reads the current time of the day by means of a system clock 119, retrieves from the table 132 the standard exercise intensities assigned to each of the time zones for the rest of the day, and defines thus retrieved standard exercise intensities as estimated exercise intensities. The resulting data is fed to a caloric consumption estimator 114 which responds to calculate a forthcoming caloric consumption necessary to make the estimated exercise intensities for the rest of the day, and calculating a forthcoming caloric balance which is the forthcoming caloric consumption minus the current caloric balance transmitted from the portable device 10.

The forthcoming caloric balance, which may be positive or negative, is then sent to an advice generator 115 which generates an advice message reflecting the forthcoming caloric balance. The advice message is transmitted together with the forthcoming balance to the portable device 10 so as to be presented on the display 20 for notifying the user of the message as well as the forthcoming caloric balance. The above function is enabled upon being requested on the side of the device 10. For generating the advice message, the advice generator 115 refers to an advice message table 135 in the data storage 130 and retrieves therefrom suitable one of the predefined advice messages in match with the forthcoming caloric balance. The data transmitted from the workstation 100 is temporarily stored in the data buffer 88 to be reviewed any time within the day.

Although not shown in FIG. 3, the processor 60 of the portable device 10 may be configured to give an assistant module which gives an assistance procedure for prompting the user to choice the kind of foods and the kind of exercises respectively in response to that the forthcoming caloric balance is negative and positive. The kinds of foods and the exercises are stored in the memory 80 in relation to its caloric consumption such that when the user choice a particular food, the assistance module calculates the intake amount of the food or the exercise time and intensity in compensation for the balance.

Figure 13:
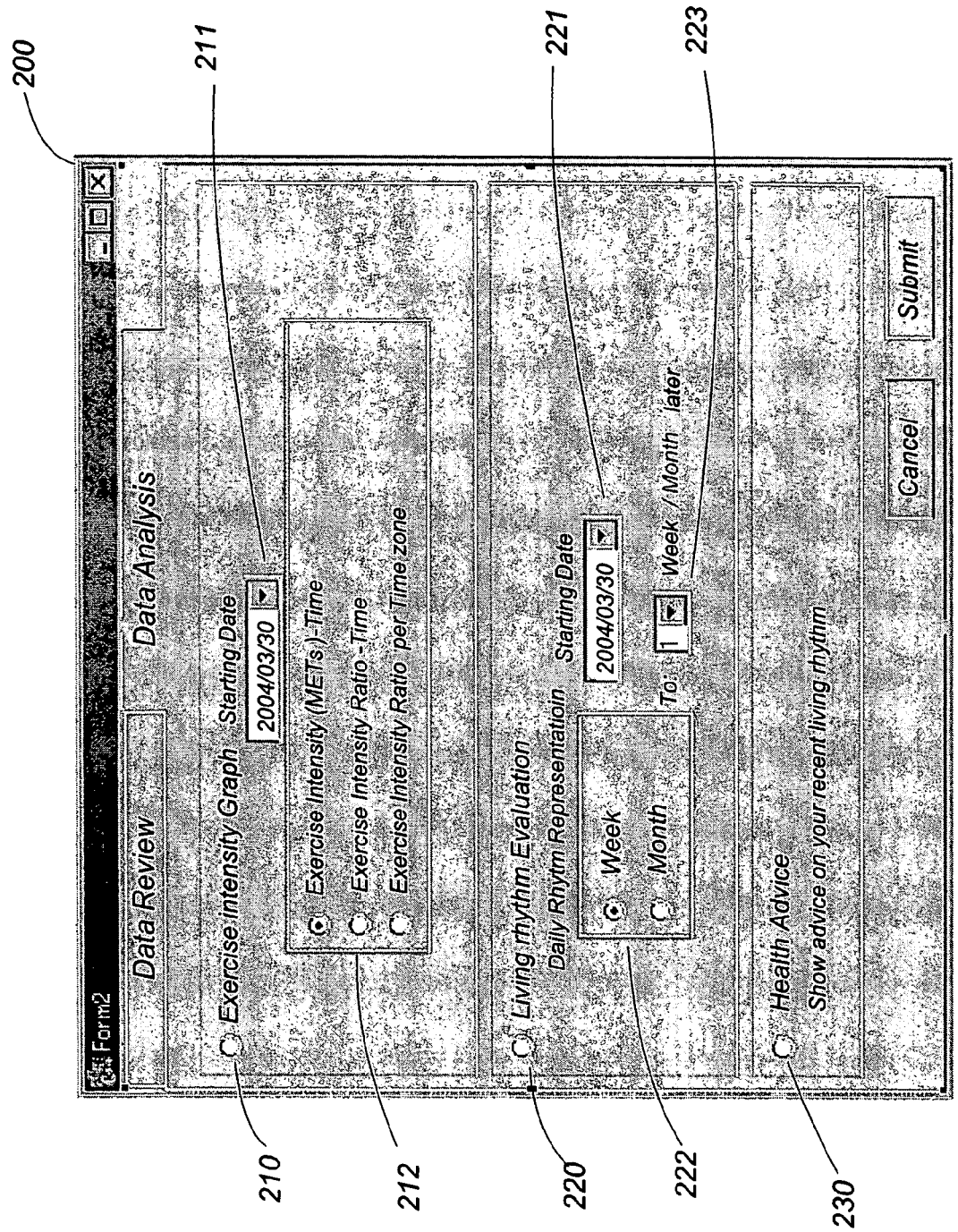
FIG. 13 illustrates a selection page which the system gives for selection between different analyses of the user's exercise.

Also referring to FIG. 11, the micro-processor 110 constitutes a report generator 116, an exercise viewer 117, and a daily activity analyzer 118 for preparing various detailed reports to be displayed on the monitor 140. The report generator 116 provides a selection page 200 in a format, as shown in FIG. 13, which leads selectively to a graphical representation of the general exercise intensities (K2) changing over a selected time period, a living rhythm evaluation, and a health advice.

Figure 14:
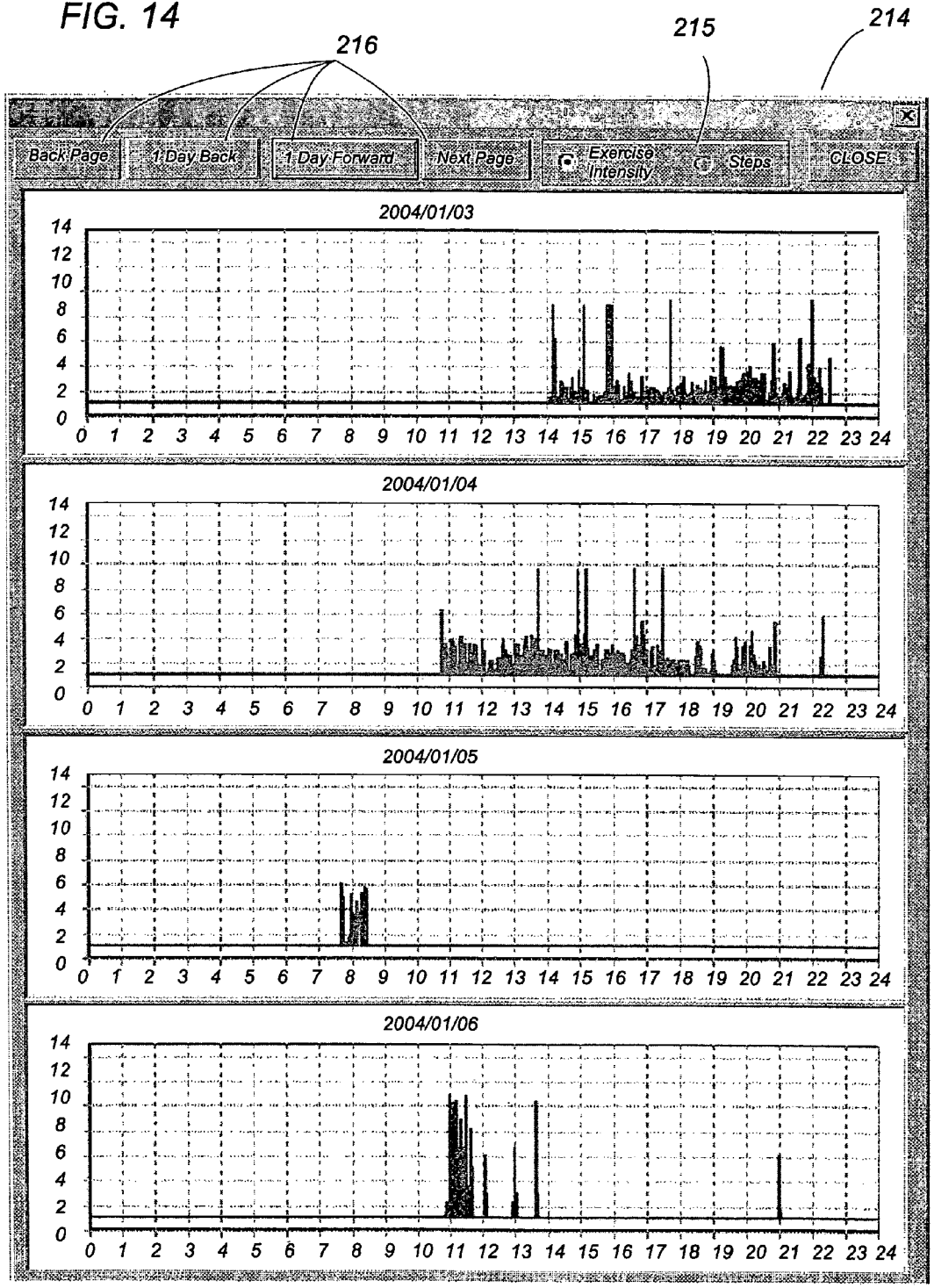
FIGS. 14 to 19 are views, respectively illustrating analytical results which the system gives in accordance with the selection at page of FIG. 13.
Figure 15:
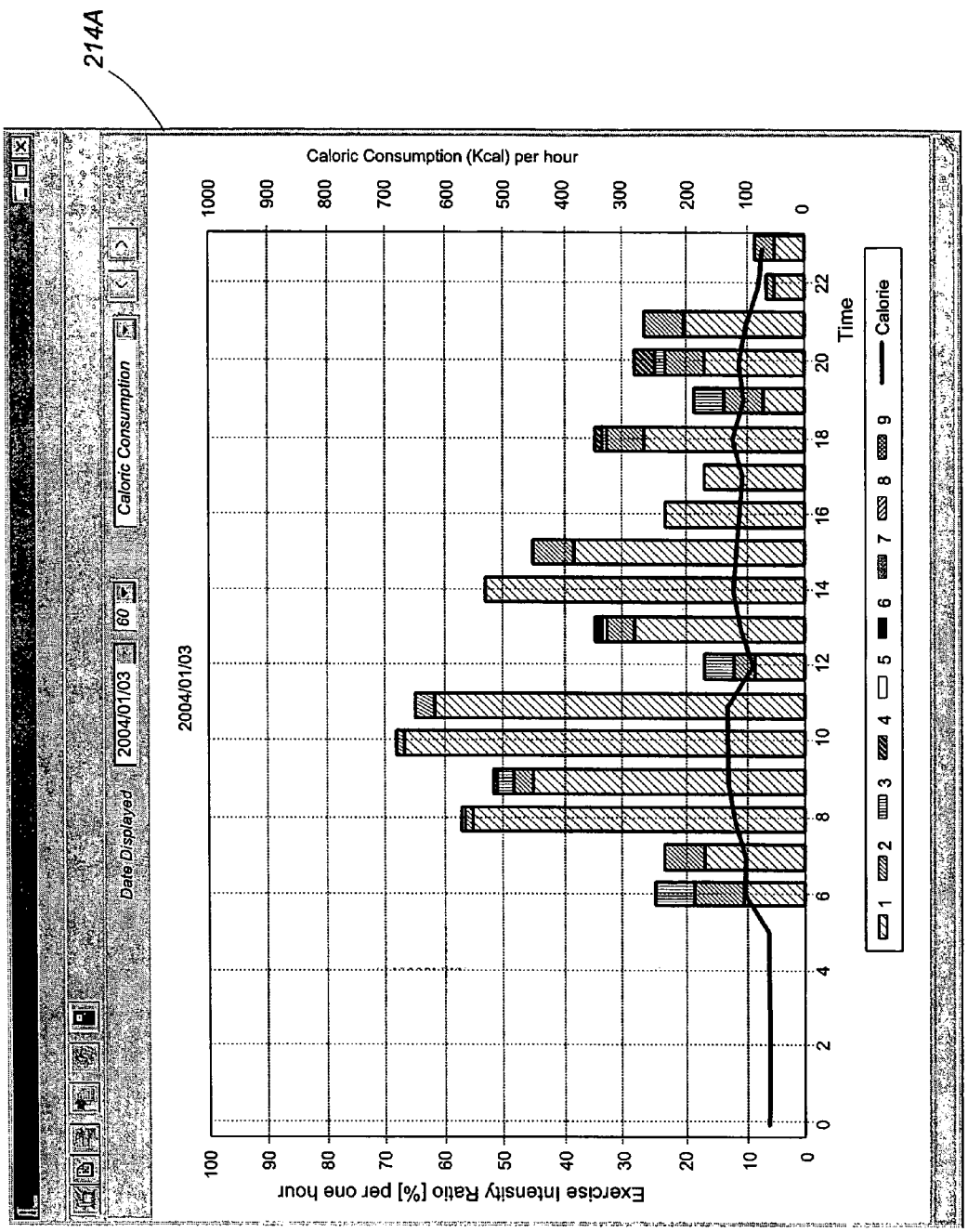
Figure 16:
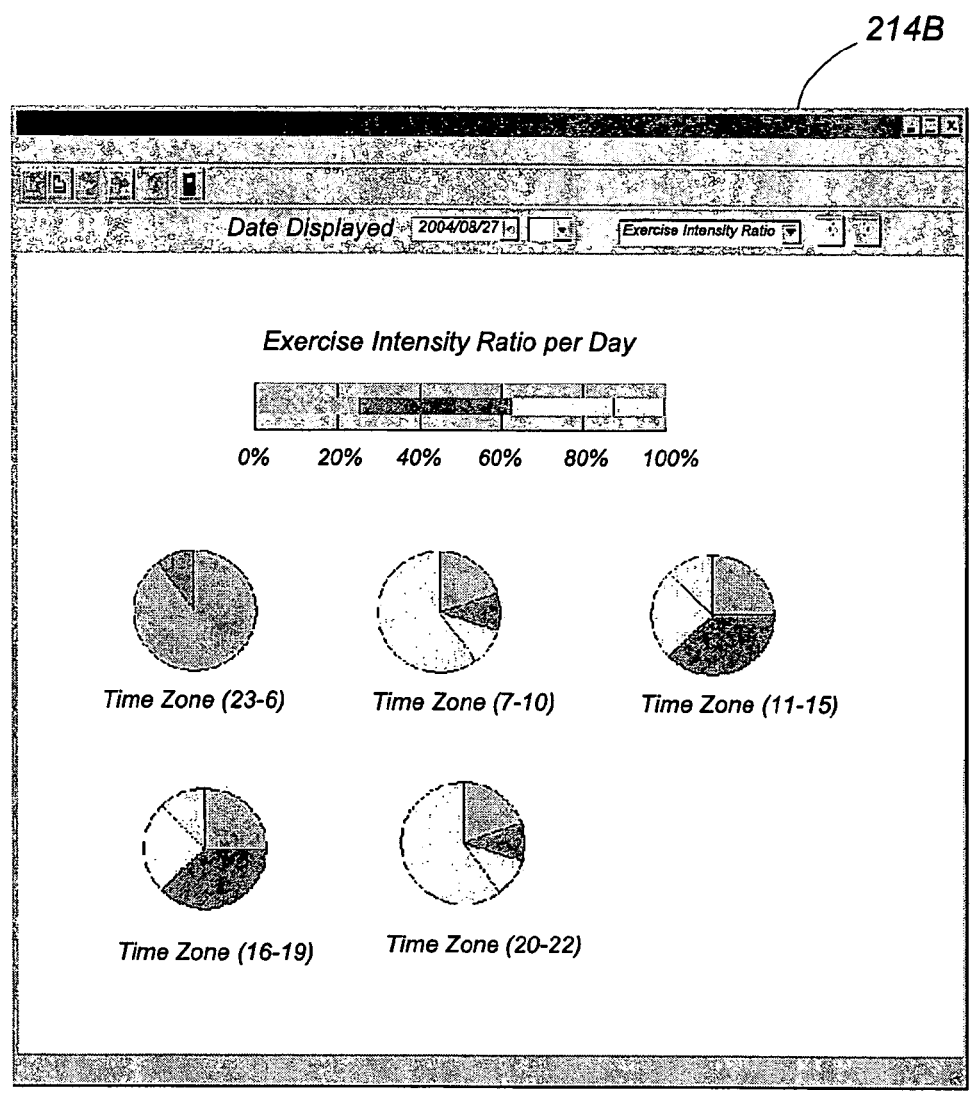

When the graphical representation is selected at a button 210 in selection page 200, the exercise viewer 117 responds to prepare, in accordance with an intended style selected at box 212, a graph of the general exercise intensities (K2) varying per one day over a selected time period, as shown in FIG. 14, to prepare a graph of the general exercise intensity ratios varying within the day over the selected time period, as shown in FIG. 15, and to prepare graphs of the general exercise intensity ratios per time zone of the selected date, as shown in FIG. 16. The time period is designated at date entry box 211 so that the exercise viewer 117 gives the corresponding data by the current date. The exercise viewer 117 collects the data set from the user data table 131 and processes the data set to present a page 214 of FIG. 14 which draws the graph of the general exercise intensities (K2) per one day. In page 214, the data is shown on a daily basis and can be scrolled back and forth to display the data of the desired date within the time period by selecting date navigation buttons 216. The exercise viewer 117 is also configured to give the number of steps per each time zone in a graphical format, which can be displayed in page 214 of FIG. 14 by selecting a corresponding entry 215. FIG. 15 shows a page 214A which the exercise viewer 117 prepares, also based upon the data set in the user data table 131, for presenting the graph of the exercise intensity ratios per one hour for each selected date within the selected time period. The exercise viewer 117 is further configured to present a line graph of the caloric consumption per one hour as well as a line graph of the number of steps per one hour on a daily basis. These line graphs are selectively displayed on the same page.

FIG. 16 shows another page 214B which the exercise viewer 117 prepares for presenting the graphs of the exercise intensity ratio per one day as well as the exercise intensity ratio per each of time zones into which one living day is divided in accordance with the activity level of the user. The system gives a plurality of time zones which can be defined by the user at a time zone definition entry 103 (FIG. 11). For example, the time zones can be defined in the manner shown in table below.

| Zone ID | Time Zone From | To | remarks |
|---|---|---|---|
| 1 | 23:00 | 6:59 | Sleep |
| 2 | 7:00 | 10:59 | Commuter time & morning activity |
| 3 | 11:00 | 15:59 | Day time activity |
| 4 | 16:00 | 19:59 | Evening activity 1 |
| 5 | 20:00 | 22:59 | Evening activity 2 |

The graphs are formatted to indicate the exercise intensity ratios per day and also per each of the time zones, preferably by giving different colors to different exercise intensities. It should be noted in this connection that the system permits the user to define the number of the time zones as well as the ranges of the individual time zones for enhanced flexibility. Thus defined time zones are stored in the user data table 131 to be retrieved as necessary.

Figure 17:
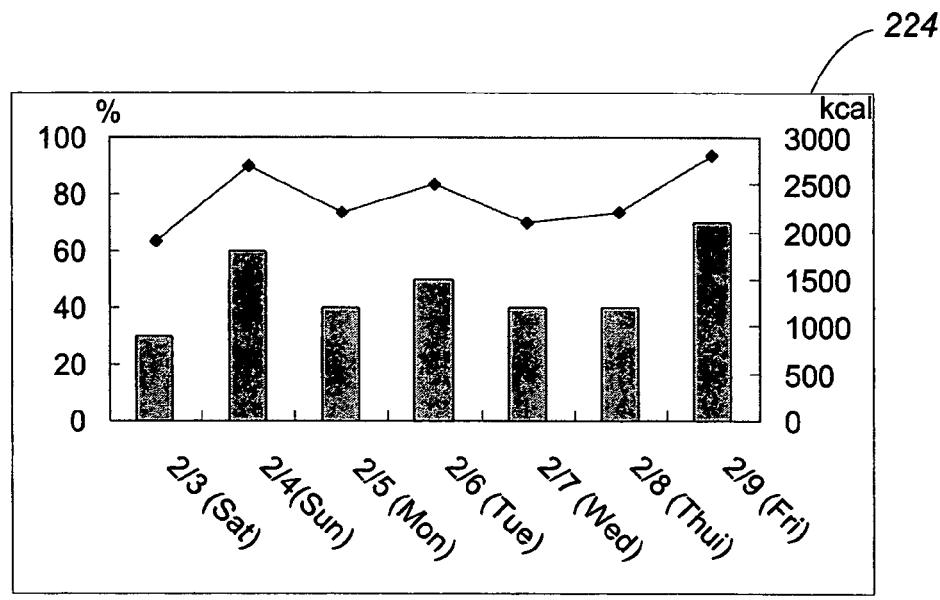

When the living rhythm evaluation is selected at a button 220 in selection page 200, the daily activity analyzer 118 collects the data set from the user data table 131 for the time period selected at date entry boxes 221, 222, and 223 in order to evaluate the daily living rhythm for the user and provide the resulting reports either on a weekly basis or on a monthly basis selected by the user. When the weekly report is selected, the analyzer 118 processes the data to obtain the total exercise intensities as well as the caloric consumption for each day, and provides the corresponding graphs in a page 224, as shown in FIG. 17. In this instance, only the general exercise intensities (K2) above a predetermined level, for example, the intensity threshold (Kt), are collected to give proportions of the exercise time resulting in thus collected exercise intensities relative to the total time of the day, thereby presenting a bar graph of thus obtained proportion for each of the day within the selected time period.

Figure 18:
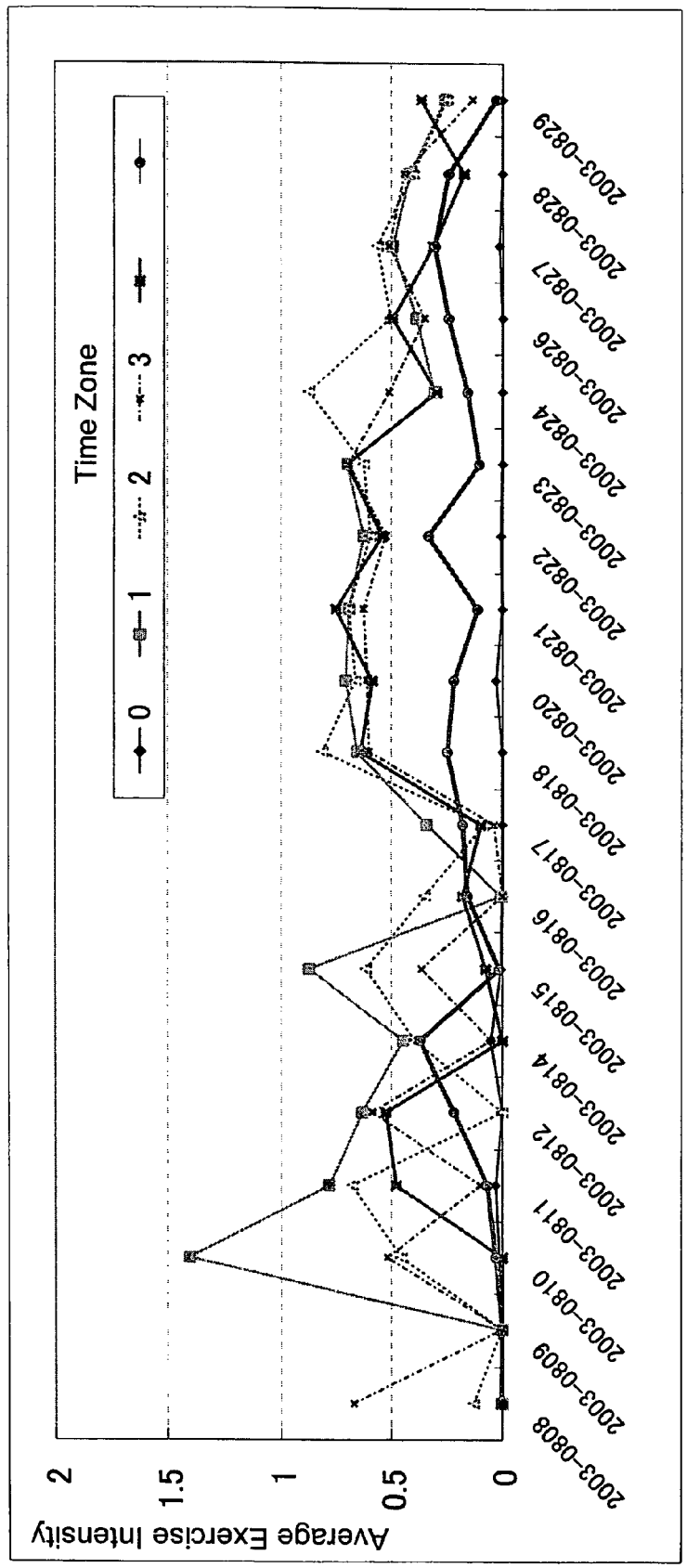

Upon selection of the monthly report, the analyzer 118 processes the data to give a daily time zone average of the exercise intensity (K2) for each of the time zones, and give corresponding line graphs as shown in FIG. 18. The daily time zone average for each time zone is obtained through the following equations (9) and (10).

$$Ah_k = \Sigma(K2)/60 \quad (9)$$

$$\Sigma Ap_i = \Sigma(Ah_k)/n \quad (10)$$

in which $\Sigma Ah_k$ is an hourly average of the general exercise intensities (K2) obtained every one minute within each time zone for each day, $\Sigma Ap_i$ is the time zone average of the exercise intensities for each time zone with (n) being the number of hours in the time zone.

Thus, the graphs of FIG. 18 offer a living rhythm with regard to each time zone over a long period of month or so.

When the health advice is selected at page 200 in FIG. 13, the daily activity analyzer 118 processes the data in order to obtain a reference average (Ravg) of the exercise intensity with regard to each of the time zones over the selected time period by means of the following equation (11) in combination with the above equations (9) and (10).

$$Ravg = \Sigma Ap_i/N \quad (11)$$

in which (N) is the number of the days included in the selected time period. Based upon the reference average (Ravg) obtained for each of the time zones, the analyzer 118 designates one specific time zone that shows a maximum activity of the user, and gets (Ravg) for the specific time zone. At the same time, the analyzer 118 obtains a daily time zone average (TZavg) of the exercise intensity with regard to the specific time zone for each of the days included within the selected time period [TZavg=$\Sigma(Ah_k)$/n]. The daily time zone average (TZavg) is then compared with the reference average (Ravg) to obtain a divergence ($\Delta$Div) therebetween by use of the following equation (12) for the specific time zone with regard to each of the day within the selected time period.

$$\Delta Div = (TZavg - Ravg)/Ravg \quad (12)$$

The resulting divergence ($\Delta$Div) is compared with predetermined criteria stored in an evaluation table 138 to give a corresponding evaluation parameter for each of the days. The criteria in the table 138 are defined as seen in a table below:

| Divergence $\Delta$Div | Evaluation parameter | Message |
|---|---|---|
| $\Delta$Div < −0.3 | −2 | Exercise Intensity lowered greatly |
| −0.3 ≤ $\Delta$Div < −0.1 | −1 | Exercise Intensity Lowered |
| −0.1 ≤ $\Delta$Div < +0.1 | 0 | Exercise Intensity Kept Constant |
| +0.1 ≤ $\Delta$Div < +0.3 | 1 | Exercise Intensity Increasing |
| +0.3 ≤ $\Delta$Div | 2 | Exercise Intensity increasing greatly |

Then, the analyzer 118 fetches a corresponding message from the table 138 for displaying the message for each day within the selected time period.

Figure 19:
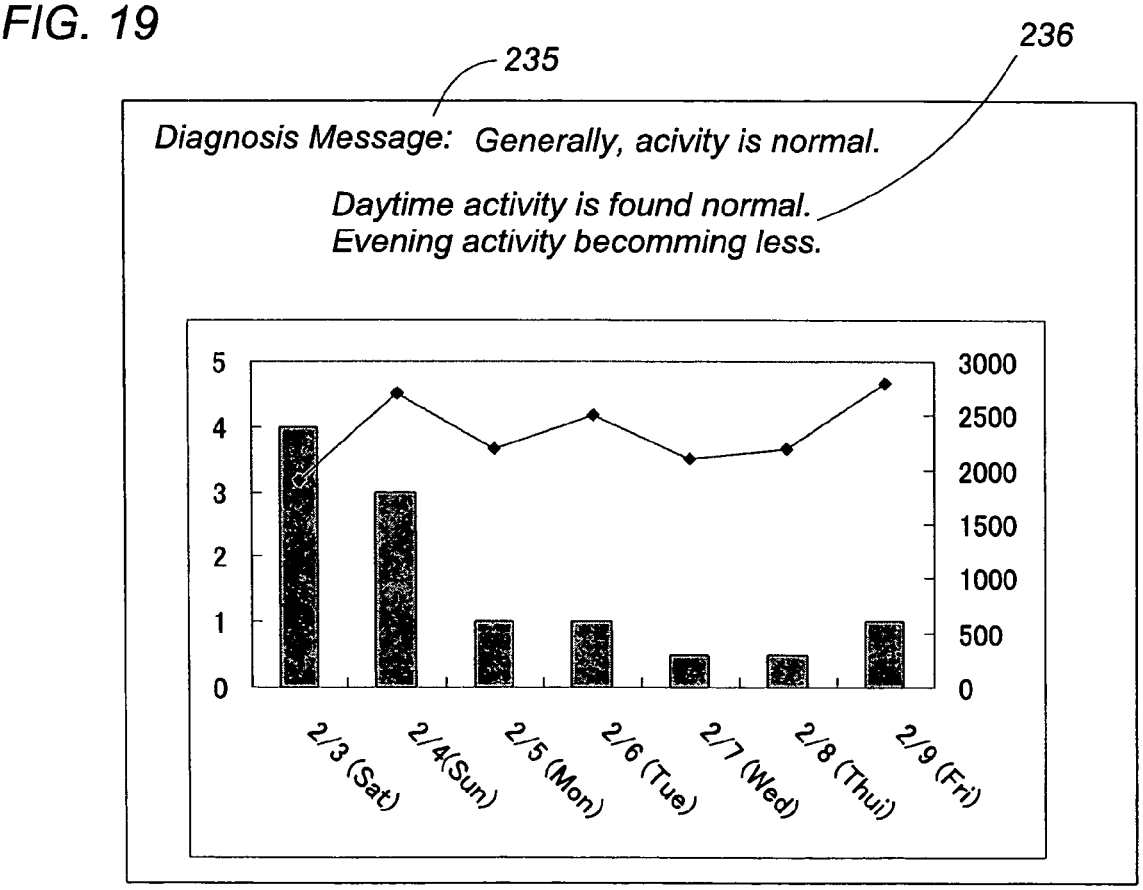

Further, the analyzer 118 collects time series of the evaluation parameters to give a tendency curve thereof for evaluation of the living rhythm, and fetches a corresponding diagnosis message from a living rhythm diagnosis message table 139. For example, the table 139 contains three basic different messages, the first one corresponding to the evaluation result that no substantial change is seen from the tendency curve, the second one corresponding to the decline of the tendency curve, and the third one corresponding to the incline of the tendency curve. The living rhythm diagnosis message 235 is displayed on the monitor 140 in combination of the graphs with regard to the general exercise intensities (K2) and the caloric consumption, as shown in FIG. 19. The graphs include a bar graph which gives, for each day within the selected time period, the total time or hour during which the general exercise intensities (K2) above the predetermined level (Kt) are detected. A line graph in the figure shows the caloric consumption for each day within the selected time period.

In addition, the analyzer 118 is configured to obtain the like divergence $\Delta$Div for each time zone in order to evaluate the exercise intensities with regard to each time zone, thereby evaluating the daily activities in details by comparing the activities in each time zone, and providing a detailed diagnosis message referring to the particular time zone which sees a substantial change in comparison with the average. The detailed diagnosis message 236 is selected from those stored in the table 139 in accordance with the evaluation result, and can be combined with the above basic message to be displayed together, as seen in FIG. 19.

Although the evaluation of the living rhythm is determined on the basis of the above defined divergence (ΔDiv), a variation of the average exercise intensities can be equally relied upon to provide like evaluation parameters.

In the above illustrated embodiment, the workstation 100 is provided separately from the portable device 10 for providing the detailed analysis and advices in the form of obvious report layouts by making the use of the abundant processing capabilities inherent to the workstation. However, one or more of the functions of the workstation 100 could be incorporated in the portable device 10 such that the portable device alone provides the one or more of the above functions. This is particularly advantageous when the portable device is configured to be combined with a cellular phone or a personal digital assistant (PDA) device having powerful processing capabilities. In this case, a camera included in the cellular phone or PDA device could be utilized as the input means or bar-code reader for entry of the kinds of the food being taken.

When the workstation 100, however, is utilized in combination with the portable device 10, the workstation may be a remote sever computer managed by a dedicated association and connected through a public computer network to the device. In this instance, the workstation or the remote server computer may be linked to a user's own personal computer to provide the reports also to the personal computer. Further, the remove server computer may be linked to computers of affiliates, such as a fitness club or diet center to which the user belongs. For example, the fitness club and the diet center receive the analytical report and data from the workstation in order to give a suitable fitness program and a suitable dietetic advice to the user, respectively.

The invention claimed is:

1. A physical activity measuring system for determining an exercise intensity of a user, said system comprising:
   a portable device configured to be carried by the user and including a processor;
   a three-axis acceleration sensor attached to said portable device and configured to sense body motions of the user to generate acceleration signals $a_x$, $a_y$, and $a_z$ in all three directions along x-axis, y-axis, and z-axis, respectively;
   an acceleration-exercise intensity relation table storing parameters ($\alpha$, $\beta$) representing a generally linear correlation between the exercise intensity and a default standard deviation of the acceleration signals sensed by said sensor; and
   an indicator mounted to said portable device for indication of the exercise intensity,
   said processor including an exercise intensity calculator for determination of an instant exercise intensity (K) of the user based upon the acceleration signals sensed by said sensor,
   said exercise calculator comprising:
      data collecting means for collecting first time-series data of said acceleration signals within a predetermined first time frame (T1);
      calculation means for calculating a first standard deviation of the first time series data of the acceleration signals using a predetermined formula defining said default standard deviation in terms of the acceleration signals in said all three directions;
      reference means for referencing to said acceleration-exercise intensity relation table to obtain said parameters $\alpha$, $\beta$ that correspond to said first standard deviation; and
      determination means which uses thus obtained parameters ($\alpha$, $\beta$) and an equation $K=\alpha \cdot Sw+\beta$ to determine said instant exercise intensity (K) where Sw is the first deviation of the acceleration signals.

2. The system as set forth in claim 1, wherein
said data collecting means is configured to collect a second time series data of said acceleration signals during each successive one of second time frame (T2) which is greater than said first time frame,
said calculation means is configured to calculate a second standard deviation of the second time series data of the acceleration signals using said predetermined formula defining said default standard deviation in terms of the acceleration signals in said all three directions,
said reference means is configured to reference to said acceleration-exercise intensity relation table to obtain said parameters ($\alpha$, $\beta$) that correspond to said second standard deviation,
said determination means is configured to uses thus obtained parameters ($\alpha$, $\beta$) and an equation $K=\alpha \cdot Sw+\beta$ to determine a general instant exercise intensity (K) where Sw is the second deviation of the acceleration signals,
said processor includes an exercise analyzer configured to receive said general exercise intensity from said exercise calculator every said second time frame to obtain a sum of the second time frames each showing the same general exercise intensity for each different ones of the general exercise intensities, and give a data set in which each different ones of the general exercise intensities is associated with the corresponding sum of the second time frame,
said device includes a data buffer which stores said instant exercise intensity and said data set of the general exercise intensity, and
said indicator includes an upper window for constant indication of said instant exercise intensity, and a lower window for indication of said data set of said general exercise intensity in a graphical format.

3. The system as set forth in claim 2, further including
a memory configured to give a history data table which stores said data set on a daily basis; and
a pager configured to retrieve said data set for a selected date from said history memory and to display the retrieved data set on said display.

4. The system as set forth in claim 2, wherein
said processor is configured to constitute
   an aerobic exercise analyzer having a predetermined intensity threshold, comparing said normal exercise intensity with said intensity threshold so as to increment a time count when said normal exercise intensity exceeds said intensity threshold, and issue an achievement signal when said time count exceeds a predetermined time threshold,
said indicator being configured to give an indication of such condition, in response to said achievement signal.

5. The system as set forth in claim 2, wherein
said processor is configured to constitute
an aerobic exercise analyzer having a predetermined intensity threshold, comparing said normal exercise intensity with said intensity threshold so as to obtain a sum of the number of the second time frames in each of which said normal exercise intensity exceeds said intensity threshold,
said indicator being configured to display said sum in association with said intensity threshold.

6. The system as set forth in claim 2, wherein
said processor is configured to give
an aerobic exercise analyzer having a predetermined intensity threshold,
said aerobic exercise calculator comparing at least one of said normal exercise intensity and said instant exercise intensity with said intensity threshold so as to increment a time count until said at least one of said normal exercise intensity and said instant exercise intensity falls below said threshold within each of time zones of the day, and store said time count for each of the associated time zones,
said display being configured to display said time count per each of said time zones.

7. The system as set forth in any one of claims 4 to 6, wherein
said aerobic exercise analyzer is configured to designate a current one of said instant exercise intensity and said normal exercise intensity as said intensity threshold.

8. The system as set forth in claim 2, wherein
said processor is configured to constitute
a clock recording a current date and time;
a BMR calculator which processes physical data of said user for obtaining a basal metabolic rate [BMR] inherent to said user; and
a caloric consumption calculator which obtains a caloric consumption which is a function of said normal exercise intensity, said basal metabolic rate [BMR], and also current time of the day;
said display being configured to display said caloric consumption on said display.

9. The system as set forth in claim 8, wherein
said caloric consumption calculator is configured to provide said caloric consumption for each of time zones of the day, and said display being configured to display said caloric consumption in association with each of said time zones.

10. The system as set forth in claim 2, further including:
a BMR calculator configured to process physical data of said user for obtaining a basal metabolic rate [BMR] inherent to said user;
food data input means configured to input food data taken by the user;
a clock recording a current date and time;
a calorie intake calculator configured to process said food data input by the current time of the day to give an accumulated caloric intake;
a caloric consumption calculator configured to obtain a current caloric consumption which is a function of said normal exercise intensity made by said current time of the day and said basal metabolic rate [BMR];
a caloric balance calculator configured to give a current caloric balance which is said accumulated caloric intake minus said current caloric consumption;
a living pattern analyzer configured to have a plurality of standard living patterns each defining a standard exercise intensity for each of time zones within a day, said living pattern analyzer analyzing said normal exercise intensity per each of said time zones in comparison with said standard living patterns so as to designate one of said standard living patterns as a specific living pattern for said user,
a living pattern reader configured to read the current time of the day and retrieve, from said specific living pattern, the standard exercise intensity as an estimated exercise intensity with regard to each of the time zones for the rest of the day,
a caloric consumption estimator configured to calculate a forthcoming caloric consumption necessary to make said estimated exercise intensities for the rest of the day, thereby determining a forthcoming caloric balance which is said forthcoming caloric consumption minus said current caloric balance; and
an advise generator which generates an advice message reflecting said forthcoming caloric balance for displaying said advice message on said display.

11. The system as set forth in claim 10, wherein
said processor is configured to give said BMR calculator, said caloric intake calculator, said caloric balance calculator, said living pattern analyzer, said living pattern reader, said caloric consumption estimator, and said advise generator.

12. The system as set forth in claim 10, further including:
a workstation provided separately from said portable device for intercommunication therewith;
said processor of said portable device being configured to constitute
said BMR calculator;
said calorie intake calculator;
said caloric consumption calculator;
said caloric balance calculator; and
a communication interface for transmitting said normal exercise intensity as well as said current caloric balance to said workstation;
said workstation comprising:
a communication interface for receiving said normal exercise intensity and said caloric balance from said processor;
said living pattern analyzer;
a system clock recording a current date and time;
said living pattern reader;
said caloric consumption estimator; and
said advice generator which transmits said advise message through said communication interface for displaying said advice message on the display of said portable device.

13. The system as set forth in claim 12, wherein
said workstation further includes:
a monitor;
a data storage configured to give a data table which stores the normal exercise intensities for each of said time zones over a plurality of days;
a term designator which designates a term defined by a start date and an end date;
a daily activity analyzer which selects one of the time zones and determines an activity level for said selected time zone based upon said exercise intensity with regard to each day included in said term, said daily activity analyzer providing a tendency of said activity level over said term, generating a living rhythm message indicating said tendency, and issuing said tendency message to be displayed on said workstation display.

14. The system as set forth in claim 12, wherein
said daily activity analyzer collects said general exercise intensities of said selected time zone for the dates included in said term and to define a reference exercise intensity as an average of the collected general exercise intensities over said term,
said daily activity analyzer comparing the general exercise intensity of said selected time zone for each of the dates within said term with said reference exercise intensity to obtain a divergence therebetween on a daily basis, and determining one of said activity levels as corresponding to thus obtained divergence so as to generate said tendency in terms of thus determined activity level.

15. The system as set forth in claim 12, wherein said daily activity analyzer generates a first living rhythm message when said tendency indicates no substantial change in said activity level, a second living rhythm message when said tendency indicates an incline of said activity level, and a third message when said tendency indicates a decline of said activity level, said first living rhythm message, said second living rhythm message, and said third living rhythm message being different from each other.

* * * * *